US006818739B2

(12) United States Patent
Sheridan et al.

(10) Patent No.: US 6,818,739 B2
(45) Date of Patent: Nov. 16, 2004

(54) SOMATOSTATINS

(75) Inventors: Mark A. Sheridan, Fargo, ND (US); Jeffrey D. Kittilson, Fargo, ND (US); Craig A. Moore, Great Falls, MT (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 09/727,739

(22) Filed: Dec. 1, 2000

(65) Prior Publication Data

US 2001/0025097 A1 Sep. 27, 2001

Related U.S. Application Data

(60) Provisional application No. 60/168,934, filed on Dec. 3, 1999.

(51) Int. Cl.[7] ............................................. C07K 14/655
(52) U.S. Cl. ..................................... 530/311; 530/399
(58) Field of Search ............................... 530/311, 399; 536/23.51; 435/7.8

(56) References Cited

U.S. PATENT DOCUMENTS

| | | | |
|---|---|---|---|
| 4,599,229 A | 7/1986 | Maccecchini | |
| 4,844,096 A | 7/1989 | Bercu | |
| 5,065,748 A | 11/1991 | Bercu | |
| 5,491,131 A | 2/1996 | Puyol et al. | |
| 5,590,656 A | 1/1997 | O'Dorisio et al. | |
| 5,681,809 A | 10/1997 | Kopchick et al. | |
| 5,763,200 A | 6/1998 | Dunmore et al. | |
| 5,846,819 A | 12/1998 | Pausch et al. | |
| 5,846,934 A | 12/1998 | Bass et al. | |
| 5,925,618 A | 7/1999 | Baumbach et al. | |

FOREIGN PATENT DOCUMENTS

EP      46669 A1  *  3/1982

OTHER PUBLICATIONS

Moore et al, Somatostatin II precursor. Database PIR, Accession No. 151064, 1996.*

Andrews et al., "Isolation and structure of a peptide hormone predicted from a mRNA sequence. A second somatostatin from the catfish pancreas," *J Biol Chem*, Aug. 25, 1981;256(16):8267–70.

Andrews et al., "Isolation of products and intermediates of pancreatic prosomatostatin processing: use of fast atom bombardment mass spectrometry as an aid in analysis of prohormone processing," *Biochemistry*, Jul. 28, 1987; 26(15):4853–61.

Andrews, et al., "Isolation and characterization of a variant somatostatin–14 and two related somatostatins of 34 and 37 residues from lamprey (*Petromyzon marinus*)," *J Biol Chem*, Oct. 25, 1988;263(30):15809–14.

Argos et al., "Nucleotide and amino acid sequence comparisons of preprosomatostatins," *J Biol Chem.*, Jul. 25, 1983; 258(14):8788–93.

Barrenechea et al., "Regulatory peptides in gastric endocrine cells of the rainbow trout *Oncorhynchus mykiss*: general distribution and colocalizations," *Tissue Cell*, Jun. 1994;26(3):309–21.

Beorlegui et al., "Endocrine cells and nerves in the pyloric ceca and the intestine of *Oncorhynchus mykiss* (Teleostei): an immunocytochemical study," *Gen Comp Endocrinol*, Jun. 1992;86(3):483–95.

Benoit et al., "Presence of somatostatin–28–(1–12) in hypothalamus and pancreas," *Proc Natl Acad Sci U S A*. Feb. 1982;79(3):917–21.

Brazeau et al., "Hypothalamic polypeptide that inhibits the secretion of immunoreactive pituitary growth hormone," *Science*, Jan. 5, 1973;179(68):77–9.

Cavanaugh et al., "Isolation and structural characterization of proglucagon–derived peptides, pancreatic polypeptide, and somatostatin from the urodele *Amphiuma tridacylum*," *Gen Comp Endocrinol*, Jan. 1996;101(1):12–20.

Celi et al., "The two nonallelic Xenopus insulin genes are expressed coordinately in the adult pancreas," *Gen Comp Endocrinol*, Aug. 1994;95(2):169–77.

Chomczynski et al., "Single–step method of RNA isolation by acid guanidinium thiocyanate–phenol–chloroform extraction," *Anal Biochem*, Apr. 1987;162(1):156–9.

Conlon et al., "Fragments of prosomatostatin isolated from a human pancreatic tumour," *Mol Cell Endocrinol*. Nov. 1984;38(1):81–6.

Conlon et al., "An elasmobranchian somatostatin: primary structure and tissue distribution in Torpedo marmorata," *Gen Comp Endocrinol*, Dec. 1985;60(3):406–13.

Conlon et al., "Structural characterization of peptides derived from prosomatostatins I and II isolated from the pancreatic islets of two species of teleostean fish: the daddy sculpin and the flounder," *Eur J Biochem*, Nov. 2, 1987;168(3):647–52.

Conlon et al., "Characterization of three peptides derived from prosomatostatin [prosomatostatin–(1–63)–, –(65–76)– and –(79–92)–peptides] in a human pancreatic tumour," *Biochem J*, Nov. 15, 1987;248(1):123–7.

Conlon et al., "Primary structures of somatostatins from the islet organ of the hagfish suggest an anomalous pathway of posttranslational processing of prosomatostatin–1," *Endocrinology*, May 1988;122(5):1855–9.

(List continued on next page.)

*Primary Examiner*—Gary Kunz
*Assistant Examiner*—Ruixiang Li
(74) *Attorney, Agent, or Firm*—Mueting, Raasch & Gebhardt, P.A.

(57) ABSTRACT

Novel somatostatin polypeptides derived from *Oncorhynchus mykiss*, polynucleotides encoding novel somatostatin polypeptides, and methods for identifying bioactive modified somatostatin polypeptides.

7 Claims, 8 Drawing Sheets

OTHER PUBLICATIONS

Conlon et al., "Somatostatin–related and glucagon–related peptides with unusual structural features from the European eel (*Anguilla anguilla*)," *Gen Comp Endocrinol*, Nov. 1988;72(2):181–9.

Conlon, "Biosynthesis of regulatory peptides—evolution aspect," *The Comparative physiology of regulatory peptides* (S. Holmgren. ed.) Chapman and Hall, London, pp. 344–369 (1989).

Conlon et al., "[Ser5]–somatostatin–14: isolation from the pancreas of a holocephalan fish, the Pacific ratfish (*Hydrolagus colliei*)," *Gen Comp Endocrinol*, Nov. 1990;80(2): 314–20.

Conlon et al., "Somatostatin– and urotensin II–related peptides: molecular diversity and evolutionary perspectives," *Regul Pept*, Mar. 26, 1997;69(2):95–103.

de Lecea et al., "A cortical neuropeptide with neuronal depressant and sleep–modulating properties," *Nature*, May 16, 1996;381(6579):242–5.

Del Sal et al., "The CTAB–DNA precipitation method: a common mini–scale preparation of template DNA from phagemids, phages or plasmids suitable for sequencing," *BioTechniques*, May 1989;7(5):514–20.

Eilertson et al., "Differential effects of somatostatin–14 and somatostatin–25 on carbohydrate and lipid metabolism in rainbow trout *Oncorhynchus mykiss*," *Gen Comp Endocrinol*, Oct. 1993;92(1):62–70.

Fujita et al., "Evolutionary aspects of "brain–gut peptides": An immunohistochemical study," *Peptides*, 1981;2(Suppl 2):123–31.

Gerich, "Somatostatin and analogues," *Diabetes Mellitus: Theory and Practice*, Ellenberg et al., eds., Medical Examinations Publishing Co., Inc., New York, NY, pp. 225–254 (1983).

Gibbins, "Co–existence and co–function," *The Comparative Physiology of Regulatory Peptides*, Holmgren, ed., Chapman and Hall, New York, NY, pp. 309–343 (1989).

Goodman et al., "Nucleotide sequence of a cloned structural gene coding for a precursor of pancreatic somatostatin" *Proc Natl Acad Sci U S A*, Oct. 1980;77(10):5869–73.

Figure 4:
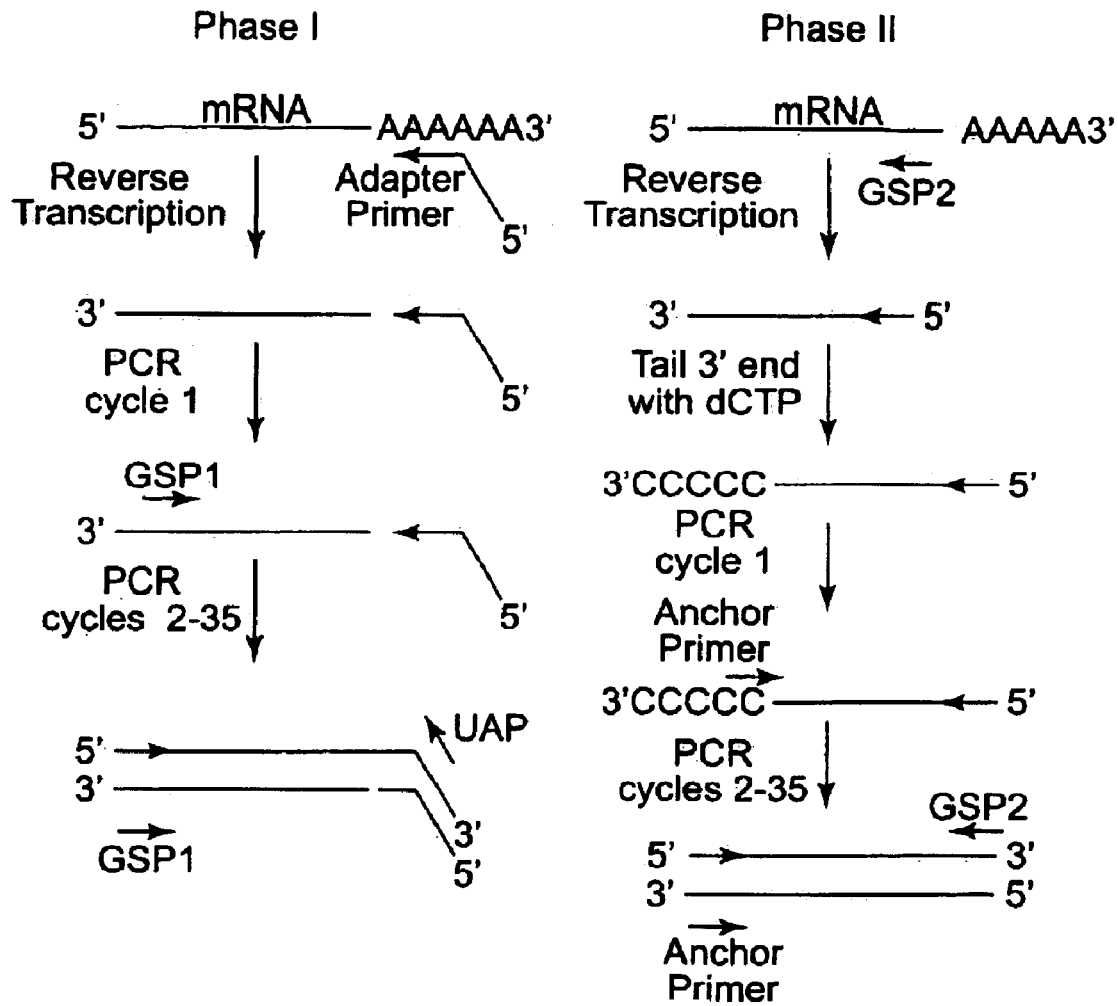

Goodman et al., Correction to Fig. 4 of "Nucleotide sequence of a cloned structural gene coding for a precursor of pancreatic somatostatin" [which originally appeared at Goodman et al., *Proc Natl Acad Sci U S A*, Oct. 1980;77(10):5869–73] *Proc Natl Acad Sci U S A*, Oct. 1980;79:1682 (1982).

Goodman et al., "Rat pre–prosomatostatin. Structure and processing by microsomal membranes," *J Biol Chem*, May 10, 1983;258(9):5570–3.

Hobart et al, "Cloning and sequence analysis of cDNAs encoding two distinct somatostatin precursors found in the endocrine pancreas of anglerfish," *Nature*, Nov. 13, 1980;288(5787):137–41.

Kittilson et al., "Polygenic expression of somatostatin in rainbow trout, *Oncorhynchus mykiss*: evidence of a preprosomatostatin encoding somatostatin–14," *Gen Comp Endocrinol*, Apr. 1999;114(1):88–96.

Lamberts et al., "The role of somatostatin and its analogs in the diagnosis and treatment of tumors," *Endocr Rev*, Nov. 1991;12(4):450–82.

Lin et al., "Expression of three distinct somatostatin messenger ribonucleic acids (mRNAs) in goldfish brain: characterization of the complementary deoxyribonucleic acids, distribution and seasonal variation of the mRNAs, and action of a somatostatin–14 variant," *Endocrinology*, May 1999;140(5):2089–99.

Magazin et al., "Sequence of a cDNA encoding pancreatic preprosomatostatin–22," *Proc Natl Acad Sci U S A*. Sep. 1982;79(17):5152–6.

Marchant et al., "Hypothalamic peptides influencing growth hormone secretion in the goldfish, *Carassius auratus*," *Fish Physiol Biochem*, 1989;7(1–4):133–9.

Minth et al.,"The structure of cloned DNA complementary to catfish pancreatic Somatostatin–14 messenger RNA," *J Biol Chem*, Sep. 10, 1982;257(17):10372–7.

Moore et al. "Isolation and characterization of a cDNA Encoding for preprosomatostatin containing [Tyr$^7$, Gly$^{10}$]–Somatostatin–14 from the endocrine pancreas of rainbow trout, *Oncorhynchus mykiss*," *Gen Comp Endocrinol*, Jun. 1995;98(3):253–61.

Moore et al., "Rainbow trout (*Oncorhynchus mykiss*) possess two somatostatin mRNAs that are differentially expressed," *Am J Physiol*. Dec. 1999;277(6 Pt 2):R1553–61.

Mullis, "The polymerase chain reaction in an anemic mode: how to avoid cold oligodeoxyribonuclear fusion," *PCR Methods Appl*, Aug. 1991;1(1):1–4.

Nguyen et al., "Characterization of the pancreatic hormones from the Brockmann body of the tilapia: Implications for islet xenograft studies," *Comp Biochem Physiol C Pharmacol Toxicol Endocrinol*, May 1995;111C(1):33–44.

Nishii et al., "Isolation and characterization of [Pro$^2$]somatostatin–14 and melanotropins from Russian sturgeon, *Acipenser gueldenstaedti* Brandt," *Gen Comp Endocrinol*, Jul. 1995;99(1):6–12.

Norman et al., "Anterior Pituitary Hormones," *Hormones*, Academic Press, New York, NY, pp. 133–68 (1997).

Norman et al., "Pancreatic Hormones: Insulin and Glucagon," *Hormones*, Academic Press, New York, NY, pp. 193–227 (1997).

Nozaki et al., "Different cellular distributions of two somatostatins in brain and pancreas of salmonids, and their associations with insulin– and glucagon–secreting cells," *Gen Comp Endocrinol*. Feb. 1988;69(2):267–80.

Ohno, "Polyploidy: Duplication of the Entire Genome," *Evolution by Gene Duplication*, Springer–Verlag, Berlin, pp. 98–106 (1970).

Patel, "General aspects of the biology and function of somatostatin," *Basic and Clinical Aspects of Neuroscience*, Weil et al., eds., Springer–Verlag, Berlin, vol. 4, pp. 1–16 (1992).

Patel et al., "The somatostatin receptor family," *Life Sci*, 1995;57(13):1249–65.

Pearse, "The phylogeny of the common peptides (Chairman's address)," *Proc R Soc Lond B Biol Sci*. 1980;210:61–62.

Pesek et al., "Fasting alters somatostatin binding to liver membranes of rainbow trout (*Oncorhynchus mykiss*)," *J Endocrinol*, Aug. 1996;150(2):179–86.

Plisetskaya et al., "Characterization of coho salmon (*Oncorhynchus kisutch*) islet somatostatins" *Gen Comp Endocrinol*, Aug. 1986;63(2):252–63.

Plisetskaya et al., Erratum to "Characterization of coho salmon (*Oncorhynchus kisutch*) islet somatostatins," [which originally appeared as Plisetskaya et al., *Gen Comp Endocrinol*, Aug. 1986;63(2):252–63] *Gen. Comp. Endocrinol.*, 1987;65(1):166.

Plisetskaya, "Pancreatic peptides," *The Comparative physiology of regulatory peptides* (S. Holmgren. ed.) Chapman and Hall, London, pp. 175–202 (1989).

Pradayrol et al., "N–terminally extended somatostatin: the primary structure of somatostatin–28," *FEBS Lett*, Jan. 1, 1980;109(1):55–8.

Pugsley, "Early stages in secretory pathway," *Protein Targeting*, Academic Press, New York, NY, pp. 45–111 (1989).

Reichlin, "Somatostatin," *Brain Peptide*, Krieger et al., eds., John Wiley and Sons, New York, NY, pp. 712–752 (1982).

Reisine et al., "Molecular biology of somatostatic receptors," *Endocr Rev*, Aug. 1995;16(4):427–42.

Sambrook et al., "Electrophoresis onto DEAE–cellulose Membrane," *Molecular Cloning: A Laboratory Manual*, $2^{nd}$ ed., Cold Spring Harbor Laboratory Press, Plainview, New York, pp. 6.24–6.27 (1989).

Sambrook et al., "Labeling the 5' terminus of DNA with bacteriophage T4 polynucleotide kinase," *Molecular Cloning: A Laboratory Manual*, $2^{nd}$ ed., Cold Spring Harbor Laboratory Press, Plainview, New York, pp. 10.59–10.60 (1989).

Shen et al., "Human somatostatin I: Sequence of the cDNA," *Proc Natl Acad Sci U S A*, Aug. 1982;79(15):4575–9.

Sheridan "Structure–function relationships of the somatostatin peptide hormone family," *Amer. Zool.*, 1998;38(5):142A (abst. 492).

Sheridan, "Regulation of lipid metabolism in poikilothermic vertebrates" *Comp Biochem Physiol*, 1994;107B(4): 495–508.

Sheridan et al., "Structure–function relationships of the signaling systems for the somatostatin peptide hormone family," *Amer. Zool.*, 2000;40(2):269–286.

Sheridan et al., "Polygenic Expression of Somatostatin in rainbow trout," *Advances in Comparative Endocrinology*, 1997;1:291–294 [Proceedings of XIII International Congress of Comparative Endocrinology Yokohama, Japan: Nov. 16–21, 1997], Kawashima et al., eds., Monduzzi Editore, Bologna, Italy.

Shuldiner et al., "RNA template–specific PCR: An improved method that dramatically reduces false positives in RT–PCR," *BioTechniques*, Dec. 1991;11(6):760–3.

Slagter et al., "Isolation and characterization of cDNAs encoding for somatostatin receptor from rainbow trout," *Amer. Zool.*, 1999;39(5):30A(abst. 170).

Spiess et al., "Isolation and characterization of somatostatin from pigeon pancreas," *Endocrinology*, Jun. 1979;76(6): 33–40.

Su et al., "Structure and evolution of somatostatin genes," *Mol Endocrinol*, Mar. 1988;2(3):209–16.

Tatusova, et al. "BLAST 2 Sequences, a new tool for comparing protein and nucleotide sequences," *FEMS Microbiol Lett*, May 15, 1999;174(2):247–50.

Tatusova, et al. *Erratum* to "BLAST 2 Sequences, a new tool for comparing protein and nucleotide sequences," [which originally appeared as Tatusova et al., *FEMS Microbiol Lett*, May 15, 1999;174(2):247–50] *FEMS Microbiol Lett* Aug. 1, 1999;177(1):187–8.

Thompson et al., "CLUSTAL W: improving the sensitivity of progressive multiple sequence alignment through sequence weighting, position–specific gap penalties and weight matrix choice," *Nucleic Acids Res*, Nov. 11, 1994;22(22):4673–80.

Tostivint et al., "Occurrence of two somatostatin variants in the frong brain: characterization of the cDNAs, distribution of the mRNAs, and receptor–binding affinities of the peptides," *Proc Natl Acad Sci U S A*, Oct. 29, 1996;93(22): 12605–10.

Travis et al., "Phenol emulsion–enhanced DNA–driven subtractive cDNA cloning: isolation of low–abundance monkey cortex–specific mRNAs," *Proc Natl Acad Sci USA*, Mar. 1988;85(5):1696–700.

Uesaka et al., "Somatostatin–, vasoactive intestinal peptide–, and granulin–like peptides isolated from intestinal extracts of goldfish, *Carassius auratus*," *Gen Comp Endocrinol*, Sep. 1995;99(3):298–306.

Vaudry et al., "Isolation of [$Pro^2$,$Met^{13}$]somatostatin–14 and somatostatin–14 from the frog brain reveals the existence of a somatostatin gene family in a tetrapod," *Biochem Biophys Res Commun*, Oct. 15, 1992;188(1):477–82.

Wang et al., "Neuroendocrine peptides (NPY, GRP, VIP, somatostatin) from the brain and stomach of the alligator," *Peptides*, May–Jun. 1993;14(3):573–9.

Wang et al., "Prosomatostatin–I is processed to somatostatin–26 and somatostatin–14 in the pancreas of the bowfin, *Amia calva*," *Regul Pept*, Aug. 13, 1993;47(1):33–9.

Wass, "Somatostatin," *Endocrinology*, DeGroot, ed., WB Saunders, Philadelphia, PA, pp. 152–166 (1989).

Yamada et al., "Cloning and functional characterization of a family of human and mouse somatostatin receptors expressed in brain, gastrointestinal tract, and kidney," *Proc Natl Acad Sci U S A*, Jan. 1, 1992;89(1):251–5.

* cited by examiner

PPSS-I

SEQ ID NO: 8    5' GGGGGGGGGGAACAGGAGCAGAACTCAAAGAGAAGCCAATCTCAACGATTGTCTGCCAATTGAACCACCTTTATCC    81

ATCCTCTGCCTCCCCGAGACCCAGAAGAAG ATG CTC TCG ACG CGT GTC CAG TGC GCC CTA GCA CTA CTC    152
                    SEQ ID NO: 3  Met Leu Ser Thr Arg Val Gln Cys Ala Leu Ala Leu Leu   -88

TCC CTA GCC CTG GCC ATC AGC AGC GTC TCT GCC GCT CCG TCC GAT GCC AAA CTC CGC CAG CTG    214
Ser Leu Ala Leu Ala Ile Ser Ser Val Ser Ala Ala Pro Ser Asp Ala Lys Leu Arg Gln Leu    -67

CTC CAA CGG TCA CTC ATG GCA CCT GCA GGC AAA CAG GAG CTT GCC AGG AAT ACA CTC GTA GAG    272
Leu Gln Arg Ser Leu Met Ala Pro Ala Gly Lys Gln Glu Leu Ala Arg Asn Thr Leu Val Glu    -46

CTA CTC TCA GAG CTC GCA CAT GTA GAG AAC GAG ATT GAA GCG ATT GAT GAC ATG TCT CAT GGC    340
Leu Leu Ser Glu Leu Ala His Val Glu Asn Glu Ile Glu Ala Ile Asp Asp Met Ser His Gly    -25

GTG GAG GAG GAT GTG GAT CTC GAG CTG GAG CTG GAG GTA CGT GCA CCC GGC CCA GTA CTG CCA CGT    403
Val Glu Glu Asp Val Asp Leu Asp Leu Glu Leu Glu Val Arg Ala Pro Gly Pro Val Leu Pro Arg    -4

GAA CGC AAG GCT GGA TGC AAG AAC TTC TTC ACA TCG TGT TAA TGAATCTACTC    466
Glu Arg Lys Ala Gly Cys Lys Asn Phe Phe Thr Lys Phe Thr Ser Cys ***

CTTTACTGTGTACTACATCTCATCTCTTTGTTCAATCATTCATTGCTGAATCCAATGCTGAATCCAATGCACCATGCCTAACCCTCCTCT    549
TCAAAAATTTAAATAAACACTGTTATAACTTAACAATCATTCTGATGTTCTATCGCTCACTTAGATTTTTTCCGAAAAG    632
GAACACAAGAAAGAATGTTCTACAAATGTATGCGGTTCTGCTTTGACTGTGATTTATGTATTATTTGGCAGACTATTTTAATTG    715
TTTGTTTGAATAAATCTGTTTCAGAACCAAAAAAAAAAAAAA    3'

Fig. 2

PPSS-II' and PPSS-II"

```
SEQ ID NO: 14  PPSS-II'  accaggcctgtcctcatacgactgatccagatcgagcatagcccggtccagtcagtctgtctcaccgcgtgcca      75
SEQ ID NO: 20  PPSS-II"  accaggcctgtcctcatacgactgatctagatcaactgatccagcacacccggtccagcttagctc****accgtgtctgg  70

Lys Cys Arg
PPSS-II'  tccctgcaaacaaaaccagctctgttgag ATG AAG GTC CGA ATC CAC CAC TGT GCC CTG GCC      139/-91
PPSS-II"  tccctgcaaacccaactcagctctgttgag ATG AGG GTC CAA ATC CAC CAC TGT GCA CTG GCC      134/-87
                                       Met Arg Val Ser Gln Ile His Cys Ala Leu Ala PPSS-II'  CTG CTG GGT TTG GCC CTG ATT TGC AGC CAA GGA GCC GCC TCG CAG CCC GAC CTG         196/-72
PPSS-II"  CTG CTG GGT CTG GCA CTG ATT TGC AGC CAA GGA GCC GCC TCG CAG CCA GAC CTG         191/-68
          Leu Leu Gly Leu Ala Leu Ile Cys Ser Gln Gly Ala Ala Ser Gln Pro Asp Leu Arg
PPSS-II'  GAC CTC CGC AGC CGC AGA CTC CTT CAG AGG GCT CGT GCC GCT GCA TTG CCA CAC AGG     253/-53
PPSS-II"  GAC CTC GCG AGC CGA CTC CTC CAG AGG GCC GCC CTG GCC GCT GCA TTG CCA CAC AGG     248/-49
          Asp Leu Ala Ser Arg Arg Leu Leu Gln Arg Ala Ala Leu Ala Ala Leu Pro His Arg PPSS-II'  AGT GGA GTA AGC GAG CGG TGG ACA TTC TAT CCC AAC TGT CCT TGC * * ***         304/-35
PPSS-II"  AGT GGA GTA AGC GAG CGA TGG ACA TTC TAT CCG AAC TGT CCT TGC CTG AGG TGG         305/-30
          Ser Gly Val Ser Glu Arg Trp Arg Phe Tyr Pro Asn Cys Pro Cys Leu Arg Trp Cys              Ala Gly             Leu Arg Val Glu
PPSS-II'  AGG CCC AGG AAA GTG AAG TGT CAA *** GCG GGG GCT AAA GAG GAC CTG CGT GTG GAG     358/-18
PPSS-II"  AGG CCC AGA AAA GTG AAG GGT CCA *** CAG CTG AAG GCC AAA GAG GAC *** *** ***     350/-14
          Arg Pro Arg Lys Val Lys Gly Pro Gln Leu Lys Ala Lys Glu Asp Gly Asn Pro Asn
PPSS-II'  CTG GAG CGC TCA GTG GTG GGC AAC CCC AAC CTT CCC CCC CGT GAG CGC AAA GCC GGC     415/+2
PPSS-II"  CTG GAG CGC TCA GTG GTG GAC *** *** AAC CTT CCC CCC CGC GAG CGC AAA GCT GGC     398/+2
          Leu Glu Arg Ser Val Asp         Asn Leu Pro Pro Arg Glu Arg Lys Ala Gly PPSS-II'  TGC AAG AAC TTC TAC AAG GGC TTC ACT TCC TGC tga gggaagaataaaccgaccacctt          477
PPSS-II"  TGC AAG AAC TTC TAC AAG GGA TTC TCT TCT TGC taa gggaagaaaagcctgaccacctt          460
          Cys Lys Asn Phe Tyr Lys Gly Phe Ser Thr Ser Cys ###

PPSS-II'  atgacatgacgctgcaatcacgtcacacctgaattacacctgacgaatgcagcaatcaacagttagctgtg         552
PPSS-II"  atgacacaatgcattcaatcacatcacacgccaaccttcatctgactgactaatgtagcaatcagcaattagctgtg     535

PPSS-II'  ccgatgatggtcttgaaatcaacagaatgatgtacctgtctaatttgaaataataaaataattg(a)n
PPSS-II"  cctgatgacaattgacaattatgatgattactgactaatttagaaataaagagaaat(a)n
```

Fig. 3

*Nucleotide Identity*

| TR II | 82.8 | 49.0 | 43.7 | 52.3 | 51.0 | 52.0 | 51.5 | 51.1 | 52.8 | 54.5 |
|---|---|---|---|---|---|---|---|---|---|---|
| 84.1 | TR I | 48.2 | 39.1 | 44.9 | 50.0 | 50.0 | 49.5 | 48.0 | 49.8 | 52.5 |
| 45.5 | 43.9 | TR I | 58.1 | 77.0 | 67.7 | 68.9 | 67.9 | 69.4 | 69.4 | 72.5 |
| 35.6 | 35.6 | 52.3 | AF I | 60.1 | 58.8 | 55.1 | 53.8 | 55.3 | 56.8 | 56.8 |
| 44.7 | 40.9 | 73.5 | 52.3 | CF I | 65.7 | 68.7 | 67.7 | 68.4 | 67.7 | 72.2 |
| 47.7 | 44.7 | 70.5 | 49.2 | 64.4 | FR I | 75.0 | 74.5 | 62.6 | 75.5 | 78.3 |
| 42.4 | 38.6 | 66.7 | 46.2 | 63.6 | 78.8 | C | 84.1 | 84.3 | 84.3 | 84.3 |
| 42.4 | 38.6 | 65.2 | 45.5 | 62.9 | 78.0 | 87.9 | R | 92.4 | 91.2 | 92.2 |
| 42.4 | 38.6 | 66.7 | 46.2 | 63.6 | 78.8 | 88.6 | 97.0 | B | 94.4 | 95.5 |
| 42.4 | 38.6 | 64.4 | 46.2 | 62.9 | 78.8 | 90.9 | 96.2 | 98.5 | M | 98.7 |
| 45.5 | 42.4 | 73.5 | 47.7 | 68.2 | 87.1 | 91.7 | 97.7 | 98.5 | 100 | H |

*Amino Acid Identity*

Fig. 5

Comparison of Amino Acid Sequences of Peptides Derived from Preprosomatostatin I[a]

| | -20 | -10 | +1 | +10 | +14 | |
|---|---|---|---|---|---|---|
| Rainbow trout[b] | | | A G C K N F F W K T F T S C | | | SEQ ID NO: 4 |
| Hagfish[d] | | A P G * * P V L A | P R E R K K A G C K N F F W K T F T S C | | | SEQ ID NO: 27 |
| Lamprey[d] | A V E R P R | Q D G Q V H E P P G R E R | A G C K N F F W K T F T S C | | | SEQ ID NO: 1 |
| Torpedo[d] | | | A G C K N F F W K T F T S C | | | SEQ ID NO: 1 |
| Ratfish[d] | | | A G C K N F F W K T F T S C | | | SEQ ID NO: 28 |
| Bowfin[d] | | S A N * * P A L A | P R E R K K A P C K N F F W K T F T S C | | | SEQ ID NO: 29 |
| Sturgeon[d] | | | A G C K * S F W K T F T S C | | | SEQ ID NO: 30 |
| Catfish[d] | | | A G C K N F F W K T F T S C | | | SEQ ID NO: 1 |
| Salmon[d] | | | A G C K N F F W K T F T S C | | | SEQ ID NO: 1 |
| Anglerfish[c] | | A A S G G P L L A | P R E R K K A G C K N F F W K T F T S C | | | SEQ ID NO: 31 |
| Eel[d] | | | A G C K N F F W K T F T S C | | | SEQ ID NO: 1 |
| Flounder[d] | | | A G C K N F F Y W K T F T S C | | | SEQ ID NO: 1 |
| Sculpin[d] | | | A G C K N F Y W K T F T S C | | | SEQ ID NO: 2 |
| Frog[c] | | | A G C K N F F W K G F T S C | | | SEQ ID NO: 1 |
| Salamander[d] | | | A G C K N F F W K T F T S C | | | SEQ ID NO: 1 |
| Alligator[d] | | | A G C K N F F W K T F T S C | | | SEQ ID NO: 1 |
| Pigeon[d] | | | A G C K N F F W K T F T S C | | | SEQ ID NO: 1 |
| Ovine[d] | | S A N S N P A M A | P R E R K K A G C K N F F W K T F T S C | | | SEQ ID NO: 32 |

Fig. 6

Sequence comparison

| | | |
|---|---|---|
| SEQ ID NO: 9 | TRII' | ---MKVCRIHCALALLGLALAICSQGAASQP------------DLDLRSRRLLQRARAAAWPHRSGVSER |
| SEQ ID NO: 15 | TRII" | ---MRVSQIHCALALLGLALAICSQGAASQP------------DLDLASRRLLQRALAAALPHRSGVSER |
| SEQ ID NO: 36 | CFII | ---MSSSPLRLALALMCLVSAVGVISCGRP-------------HVVLNSALEEARNVPFGEEVPERLT |
| SEQ ID NO: 37 | AFII | ---MQCIRCPAILALLALVLCGPSVSSQLDREQSDNQDLDLELRQHWLLERARSAGLLSQBWSKRA |
| SEQ ID NO: 38 | GFII | ---MRLCELHCYLALLGLSLVLCGRCANSQL-EP---------DLDFRHHRLLQRASATGQATQDFTKRD |
| SEQ ID NO: 39 | GFIII | ------MQLLSSLVSLLLVLYSVRAAAVL--------------PVEERNPAQSRELSKE-RKELILKL |
| SEQ ID NO: 40 | FRII | ------MLGSAGTLLLLLLAW-GARALSQ--------------PDDNRITTGRNQDLNAIQQDLLLKL |
| SEQ ID NO: 3 | TRI | ---MLSTRVQCALALLSLALAISSVSAAPS-------------DAKLRQLLQRSLMAPAGKQELARNT |
| SEQ ID NO: 41 | CFI | ---MPSTRIQCALALLAVALSVCSVSGAPS-------------DAKLRQFLQRSILAPSVKQELTRYT |
| SEQ ID NO: 42 | AFI | MKMVSSSRLRCLLVLLLSLTASISCSFAGQR-------------DSKIRLLLHRYPLQGS-KQDMTRSA |
| SEQ ID NO: 43 | GFI | ---MLSTRIQCALALLSLALAVCSVSAAPT-------------DAKLRQLLQRSLLNPAGKQELARYT |
| SEQ ID NO: 44 | FRI | ---MQSCRVQCALTLLSLALAINSISAAPT-------------DPRLRQFLQKSLASAG-KQELAKYF |
| SEQ ID NO: 45 | C | ---MLSCRIQCALALLSIALAVGTVSAAPS-------------DPRLRQFLQKSLAAAAGKQELAKYF |
| SEQ ID NO: 46 | R | ---MLSCRLQCALAALCIVLALGGVTGAPS-------------DPRLRQFLQKSLAATGKQELAKYF |
| SEQ ID NO: 47 | B | ---MLSCRLQCALAALSIVLALGGVTGAPS-------------DPRLRQFLQKSLAAAAGKQELAKYF |
| SEQ ID NO: 48 | M | ---MLSCRLQCALAALSIVLALGCVTGAPS-------------DPRLRQFLQKSLAAAAGKQELAKYF |
| SEQ ID NO: 49 | H | ---MLSCRLQCALAALSIVLALGCVTGAPS-------------DPRLRQFLQKSLAAAAGKQELAKYF |

(continued)

```
WRTFYPNCPCLR--PRKVKCP-AGAKE-DLR--VELERSVGN-PNNLPPRERKAGCKNFYWKGFTSC
WRTFYPNCPCLRWRPRKVKGPQLKAKE-DL------ERSV---DNLPPRERKAGCKNFYWKGFTSC
LPELQW-MLSNNELTPVQVERAPRS-------RLELVRRDN----T-VTSKPLNCMNYFWKSRTAC
VEELLAQMSLPEATFQREAEDASMATE-G---RMNLERSVDS-TNNLPPRERKAGCKNFYWKGFTSC
VEKLLSLLSIPEMEMR--EKGLSMAGE-SEDLRLBQERSAES-SNQLPTRVRKEGCKNFYWKGFTSC
ISGLLID--GVDNSVLDGEIAPVPFDAEEPLESRLE-ERAVYNRLSQLPQRDRKAPCKNFFWKTFTSC
LSGWTD--S-RESNLVEVERNVPDPE-P----KIPPSVK--FPRLSLRERKAPCKNFFWKTFTMC
LVELLS-ELAHVENEAIELDDMSHGVE-QEDVDLELERAPG--PVLAPRERKAGCKNFFWKTFTSC
LARLLA-ELAEAENEVLDSDEVSRAAE-SEGARLEMERAAG--PMLAPRERKAGCKNFFWKTFTSC
LAELLLSDLLQGENEALEEENFPLAEGGPEDAHADLBRAASG-GPLLAPRERKAGCKNFFWKTFTSC
LADLLS-ELVQAENEALEPEDLSRAVE-KDEVRLELERAAG--PMLAPRERKAGCKNFFWKTFTSC
LAELLS-BPSQTDNEALESDDLPRGAE-QDEVRLELBRSANS-SPALAPRERKAGCKNFFWKTFTSC
LAELLS-EPSQTBNEALESEDLSRGAE-QDEVRLELERSANS-NPALAPRERKAGCKNFFWKTFTSC
LAELLS-EPSQTNEALEPEDLPQAAE-QDEMRLELQRSANS--NPAMAPRERKAGCKNFFWKTFTSC
LAELLS-EPNQTBIDALEPEDLSQAAE-QDEMRLELQRSANS--NPAMAPRERKAGCKNFFWKTFTSC
LAELLS-EPNQTENDALEPEDLSQAAE-QDEMRLELQRSANS--NPAMAPRERKAGCKNFFWKTFTSC
LAELLS-EPNQTENDALEPEDLSQAAE-QDEMRLELQRSANS--NPAMAPRERKAGCKNFFWKTFTSC
LAELLS-EPNQTENDALEPEDLSQAAE-QDEMRLBLQRSANS--NPAMAPRERKAGCKNFFWKTFTSC
```

Fig. 7

SEQUENCE LISTING

<160> NUMBER OF SEQ ID NOS: 52

<210> SEQ ID NO 1
<211> LENGTH: 14
<212> TYPE: PRT

```
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 14
<212> TYPE: PRT
<213> ORGANISM: Oncorhynchus mykiss

<400> SEQUENCE: 2

Ala Gly Cys Lys Asn Phe Tyr Trp Lys Gly Phe Thr Ser Cys
1               5                   10

<210> SEQ ID NO 3
<211> LENGTH: 114
<212> TYPE: PRT
<213> ORGANISM: Oncorhynchus mykiss

<400> SEQUENCE: 3

Met Leu Ser Thr Arg Val Gln Cys Ala Leu Ala Leu Leu Ser Leu Ala
1               5                   10                  15

Leu Ala Ile Ser Ser Val Ser Ala Ala Pro Ser Asp Ala Lys Leu Arg
            20                  25                  30

Gln Leu Leu Gln Arg Ser Leu Met Ala Pro Ala Gly Lys Gln Glu Leu
        35                  40                  45

Ala Arg Asn Thr Leu Val Glu Leu Leu Ser Glu Leu Ala His Val Glu
    50                  55                  60

Asn Glu Ala Ile Glu Leu Asp Asp Met Ser His Gly Val Glu Gln Glu
65                  70                  75                  80

Asp Val Asp Leu Glu Leu Glu Arg Ala Pro Gly Pro Val Leu Ala Pro
                85                  90                  95

Arg Glu Arg Lys Ala Gly Cys Lys Asn Phe Phe Trp Lys Thr Phe Thr
            100                 105                 110

Ser Cys

<210> SEQ ID NO 4
<211> LENGTH: 26
<212> TYPE: PRT
<213> ORGANISM: Oncorhynchus mykiss

<400> SEQUENCE: 4

Ala Pro Gly Pro Val Leu Ala Pro Arg Glu Arg Lys Ala Gly Cys Lys
1               5                   10                  15

Asn Phe Phe Trp Lys Thr Phe Thr Ser Cys
            20                  25

<210> SEQ ID NO 5
<211> LENGTH: 88
<212> TYPE: PRT
<213> ORGANISM: Oncorhynchus mykiss

<400> SEQUENCE: 5

Met Leu Ser Thr Arg Val Gln Cys Ala Leu Ala Leu Leu Ser Leu Ala
1               5                   10                  15

Leu Ala Ile Ser Ser Val Ser Ala Ala Pro Ser Asp Ala Lys Leu Arg
            20                  25                  30

Gln Leu Leu Gln Arg Ser Leu Met Ala Pro Ala Gly Lys Gln Glu Leu
        35                  40                  45
```

```
Ala Arg Asn Thr Leu Val Glu Leu Leu Ser Glu Leu Ala His Val Glu
        50                  55                  60

Asn Glu Ala Ile Glu Leu Asp Asp Met Ser His Gly Val Glu Gln Glu
65                  70                  75                  80

Asp Val Asp Leu Glu Leu Glu Arg
                85

<210> SEQ ID NO 6
<211> LENGTH: 12
<212> TYPE: PRT
<213> ORGANISM: Oncorhynchus mykiss

<400> SEQUENCE: 6

Ala Pro Gly Pro Val Leu Ala Pro Arg Glu Arg Lys
1               5                   10

<210> SEQ ID NO 7
<211> LENGTH: 24
<212> TYPE: PRT
<213> ORGANISM: Oncorhynchus mykiss

<400> SEQUENCE: 7

Met Leu Ser Thr Arg Val Gln Cys Ala Leu Ala Leu Leu Ser Leu Ala
1               5                   10                  15

Leu Ala Ile Ser Ser Val Ser Ala
            20

<210> SEQ ID NO 8
<211> LENGTH: 763
<212> TYPE: DNA
<213> ORGANISM: Oncorhynchus mykiss

<400> SEQUENCE: 8
gggggggggg gaacaggagc agcagaactc aaagagaagc caatctcaac gattgtctgc      60
ccaattgaac cacctttatc catcctctgc ctcccccgag acccagaaga agatgctctc     120
gacgcgtgtc cagtgcgccc tagcactact ctccctagcc ctggccatca gcagcgtctc     180
tgccgctccg tccgatgcca aactccgcca gctgctccaa cggtcactca tggcacctgc     240
aggcaaacag gagcttgcca ggaatacact cgtagagcta ctctcagagc tcgcacatgt     300
agagaacgag gcgattgaat ggatgacat gtctcatggc gtggagcagg aggatgtgga     360
tctcgagctg gagcgtgcac ccggcccagt actggctcca cgtgaacgca aggctggatg     420
caagaacttc ttctggaaga cctttacatc gtgttaatga atctactcct ttactgtgtg     480
tactacatct catctctttt gtttcaatca ctcattgctg aatccaatgc accatggcct     540
aaccctcctc ttcaaaaaat ttaaataaac actgttataa ctttaacaat cattctgatg     600
tttctatcgc tcacttagat ttttttccga aaggaacac aagaaagaat gttctacaaa      660
tgtatgcggt tctgctttga ctgtgattta tgtattttgg cagactattt ttaattgttt     720
gtttgaataa aatctgtgtt tcagaaccaa aaaaaaaaa aaa                        763

<210> SEQ ID NO 9
<211> LENGTH: 115
<212> TYPE: PRT
<213> ORGANISM: Oncorhynchus mykiss

<400> SEQUENCE: 9

Met Lys Val Cys Arg Ile His Cys Ala Leu Ala Leu Leu Gly Leu Ala
1               5                   10                  15
```

```
Leu Ala Ile Cys Ser Gln Gly Ala Ala Ser Gln Pro Asp Leu Asp Leu
            20                  25                  30

Arg Ser Arg Arg Leu Leu Gln Arg Ala Arg Ala Ala Ala Leu Pro His
        35                  40                  45

Arg Ser Gly Val Ser Glu Arg Trp Arg Thr Phe Tyr Pro Asn Cys Pro
    50                  55                  60

Cys Leu Arg Pro Arg Lys Val Lys Cys Pro Ala Gly Ala Lys Glu Asp
65                  70                  75                  80

Leu Arg Val Glu Leu Glu Arg Ser Val Gly Asn Pro Asn Asn Leu Pro
                85                  90                  95

Pro Arg Glu Arg Lys Ala Gly Cys Lys Asn Phe Tyr Trp Lys Gly Phe
            100                 105                 110

Thr Ser Cys
        115

<210> SEQ ID NO 10
<211> LENGTH: 28
<212> TYPE: PRT
<213> ORGANISM: Oncorhynchus mykiss

<400> SEQUENCE: 10

Ser Val Gly Asn Pro Asn Asn Leu Pro Pro Arg Glu Arg Lys Ala Gly
1               5                   10                  15

Cys Lys Asn Phe Tyr Trp Lys Gly Phe Thr Ser Cys
            20                  25

<210> SEQ ID NO 11
<211> LENGTH: 87
<212> TYPE: PRT
<213> ORGANISM: Oncorhynchus mykiss

<400> SEQUENCE: 11

Met Lys Val Cys Arg Ile His Cys Ala Leu Ala Leu Leu Gly Leu Ala
1               5                   10                  15

Leu Ala Ile Cys Ser Gln Gly Ala Ala Ser Gln Pro Asp Leu Asp Leu
            20                  25                  30

Arg Ser Arg Arg Leu Leu Gln Arg Ala Arg Ala Ala Ala Leu Pro His
        35                  40                  45

Arg Ser Gly Val Ser Glu Arg Trp Arg Thr Phe Tyr Pro Asn Cys Pro
    50                  55                  60

Cys Leu Arg Pro Arg Lys Val Lys Cys Pro Ala Gly Ala Lys Glu Asp
65                  70                  75                  80

Leu Arg Val Glu Leu Glu Arg
                85

<210> SEQ ID NO 12
<211> LENGTH: 14
<212> TYPE: PRT
<213> ORGANISM: Oncorhynchus mykiss

<400> SEQUENCE: 12

Ser Val Gly Asn Pro Asn Asn Leu Pro Pro Arg Glu Arg Lys
1               5                   10

<210> SEQ ID NO 13
<211> LENGTH: 25
<212> TYPE: PRT
<213> ORGANISM: Oncorhynchus mykiss
```

-continued

<400> SEQUENCE: 13

Met Lys Val Cys Arg Ile His Cys Ala Leu Ala Leu Leu Gly Leu Ala
1               5                   10                  15

Leu Ala Ile Cys Ser Gln Gly Ala Ala
            20                  25

<210> SEQ ID NO 14
<211> LENGTH: 623
<212> TYPE: DNA
<213> ORGANISM: Oncorhynchus mykiss

<400> SEQUENCE: 14

```
accaggcctg ctccataccg actgatccag atcgagcata gcccggtcca gctcagctcg      60
tctcaccgcg tgccatccct gcaaacaaaa cccagctctg ttggagatga aggtctgccg     120
aatccactgt gccctggccc tgctgggttt ggccctggcc atttgcagcc aaggagccgc     180
ctcgcagccc gacctggacc tccgcagccg cagactcctt cagagggctc gtgccgctgc     240
attgccacac aggagtggag taagcgagcg gtggaggaca ttctatccca actgtccttg     300
cctgaggccc aggaaagtga agtgtcaagc gggggctaaa gaggacctgc gtgtggagct     360
ggagcgctca gtgggcaacc ccaacaacct tcccccccgt gagcgcaaag ccggctgcaa     420
gaacttctac tggaagggct tcacttcctg ctgagggaag aataaaccga ccaccttatg     480
acatgacgct gccaatcacg tcacaccgcc aacttacacc tgacgaatgc agccaatcaa     540
cagttagctg tgcccgatga tggttcttga aatcaacaga atgatgtacc tgtctaattt     600
gtgaaataaa tataaaataa ttg                                             623
```

<210> SEQ ID NO 15
<211> LENGTH: 111
<212> TYPE: PRT
<213> ORGANISM: Oncorhynchus mykiss

<400> SEQUENCE: 15

Met Arg Val Ser Gln Ile His Cys Ala Leu Ala Leu Leu Gly Leu Ala
1               5                   10                  15

Leu Ala Ile Cys Ser Gln Gly Ala Ala Ser Gln Pro Asp Leu Asp Leu
            20                  25                  30

Ala Ser Arg Arg Leu Leu Gln Arg Ala Leu Ala Ala Ala Leu Pro His
        35                  40                  45

Arg Ser Gly Val Ser Glu Arg Trp Arg Thr Phe Tyr Pro Asn Cys Pro
    50                  55                  60

Cys Leu Arg Trp Arg Pro Arg Lys Val Lys Gly Pro Gln Leu Lys Ala
65                  70                  75                  80

Lys Glu Asp Leu Glu Arg Ser Val Asp Asn Leu Pro Pro Arg Glu Arg
                85                  90                  95

Lys Ala Gly Cys Lys Asn Phe Tyr Trp Lys Gly Phe Thr Ser Cys
            100                 105                 110

<210> SEQ ID NO 16
<211> LENGTH: 25
<212> TYPE: PRT
<213> ORGANISM: Oncorhynchus mykiss

<400> SEQUENCE: 16

Ser Val Asp Asn Leu Pro Pro Arg Glu Arg Lys Ala Gly Cys Lys Asn
1               5                   10                  15

Phe Tyr Trp Lys Gly Phe Thr Ser Cys
            20                  25

```
                20                  25

<210> SEQ ID NO 17
<211> LENGTH: 86
<212> TYPE: PRT
<213> ORGANISM: Oncorhynchus mykiss

<400> SEQUENCE: 17

Met Arg Val Ser Gln Ile His Cys Ala Leu Ala Leu Leu Gly Leu Ala
1               5                   10                  15

Leu Ala Ile Cys Ser Gln Gly Ala Ala Ser Gln Pro Asp Leu Asp Leu
            20                  25                  30

Ala Ser Arg Arg Leu Leu Gln Arg Ala Leu Ala Ala Leu Pro His
        35                  40                  45

Arg Ser Gly Val Ser Glu Arg Trp Arg Thr Phe Tyr Pro Asn Cys Pro
    50                  55                  60

Cys Leu Arg Trp Arg Pro Arg Lys Val Lys Gly Pro Gln Leu Lys Ala
65                  70                  75                  80

Lys Glu Asp Leu Glu Arg
                85

<210> SEQ ID NO 18
<211> LENGTH: 11
<212> TYPE: PRT
<213> ORGANISM: Oncorhynchus mykiss

<400> SEQUENCE: 18

Ser Val Asp Asn Leu Pro Pro Arg Glu Arg Lys
1               5                   10

<210> SEQ ID NO 19
<211> LENGTH: 25
<212> TYPE: PRT
<213> ORGANISM: Oncorhynchus mykiss

<400> SEQUENCE: 19

Met Arg Val Ser Gln Ile His Cys Ala Leu Ala Leu Leu Gly Leu Ala
1               5                   10                  15

Leu Ala Ile Cys Ser Gln Gly Ala Ala
            20                  25

<210> SEQ ID NO 20
<211> LENGTH: 600
<212> TYPE: DNA
<213> ORGANISM: Oncorhynchus mykiss

<400> SEQUENCE: 20
accaggcctg ctccatatca actgatctag atccagcaca ccccggtcca gcttagctca    60
ccgtgtctgg tccctgcaaa cccaactcag ctctgttgga gatgagggtc tcccaaatcc   120
actgtgcact ggccctgctg gtctggccc tggcaatttg cagccaagga gccgcctcgc    180
agccagacct ggacctcgcg agccgccgac tcctccagag ggccctggcc gctgcattgc   240
cacacaggag tggagtaagc gagcgatgga ggacattcta tccgaactgt ccttgcctga   300
ggtggaggcc cagaaaagtg aagggtccac agctgaaggc caagaggac ctggagcgct    360
cagtggacaa ccttcccccc cgcgagcgca agctggctg caagaacttc tactggaagg    420
gattcacttc ttgctaaggg aagaaaagcc tgaccacctt atgacacaat gcattcaatc   480
acatcacacc gccaaccttc atctgactaa tgtagccaat cagcaattag ctgtgcctga   540
```

```
tgacaattat gattatgatg tacctgacta atttagaaat aaagagaaat aaagagaaac        600
```

```
<210> SEQ ID NO 21
<211> LENGTH: 28
<212> TYPE: PRT
<213> ORGANISM: Homo sapiens

<400> SEQUENCE: 21

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
ggccacgcgt cgactagtac tttttttttt ttttttt                                37

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23
cuacuacuac uaggccacgc gtcgactagt ac                                     32

<210> SEQ ID NO 24
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (36)..(37)
<223> OTHER INFORMATION: i
<220> FEATURE:
<221> NAME/KEY: modified_base
<222> LOCATION: (41)..(42)
<223> OTHER INFORMATION: i
<220> FEATURE:
<221> NAME/KEY: modified_base
<222> LOCATION: (46)..(47)
<223> OTHER INFORMATION: i

<400> SEQUENCE: 24
cuacuacuac uaggccacgc gtcgactagt acgggnnggg nngggnng                    48

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aagaacttct tctggaagac                                                   20

<210> SEQ ID NO 26
<211> LENGTH: 20
```

<212> TYPE: DNA
<213> ORGANISM: Artificial Sequence
<220> FEATURE:
<223> OTHER INFORMATION: Primer

<400> SEQUENCE: 26
attcattaac acgatgtaaa                                                                                  20

<210> SEQ ID NO 27
<211> LENGTH: 33
<212> TYPE: PRT
<213> ORGANISM: Myxine glutinosa

<400> SEQUENCE: 27

Ala Val Glu Arg Pro Arg Gln Asp Gly Gln Val His Glu Pro Pro Gly
1               5                   10                  15

Arg Glu Arg Lys Ala Gly Cys Lys Asn Phe Phe Trp Lys Thr Phe Thr
            20                  25                  30

Ser

<210> SEQ ID NO 28
<211> LENGTH: 14
<212> TYPE: PRT
<213> ORGANISM: Hydrolagus collei

<400> SEQUENCE: 28

Ala Gly Cys Lys Ser Phe Phe Trp Lys Thr Phe Thr Ser Cys
1               5                   10

<210> SEQ ID NO 29
<211> LENGTH: 26
<212> TYPE: PRT
<213> ORGANISM: Amia calva

<400> SEQUENCE: 29

Ser Ala Asn Pro Ala Leu Ala Pro Arg Glu Arg Lys Ala Gly Cys Lys
1               5                   10                  15

Asn Phe Phe Trp Lys Thr Phe Thr Ser Cys
            20                  25

<210> SEQ ID NO 30
<211> LENGTH: 14
<212> TYPE: PRT
<213> ORGANISM: Acipenser gueldenstaedti

<400> SEQUENCE: 30

Ala Pro Cys Lys Asn Phe Phe Trp Lys Thr Phe Thr Ser Cys
1               5                   10

<210> SEQ ID NO 31
<211> LENGTH: 28
<212> TYPE: PRT
<213> ORGANISM: Lophius americanus

<400> SEQUENCE: 31

Ala Ala Ser Gly Gly Pro Leu Leu Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 32
<211> LENGTH: 28
<212> TYPE: PRT

```
<213> ORGANISM: Sus scrofa

<400> SEQUENCE: 32

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ggctgcaaga atttcttctc g                                              21

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
gttggcggtg tgacgtgatt g                                              21

<210> SEQ ID NO 35
<211> LENGTH:
<212> TYPE:
<213> ORGANISM:

<400> SEQUENCE: 35

000

<210> SEQ ID NO 36
<211> LENGTH: 105
<212> TYPE: PRT
<213> ORGANISM: Ictalrus punctatus

<400> SEQUENCE: 36

Met Ser Ser Ser Pro Leu Arg Leu Ala Leu Ala Leu Met Cys Leu Val
1               5                   10                  15

Ser Ala Val Gly Val Ile Ser Cys Gly Arg Pro His Val Val Leu Asn
            20                  25                  30

Ser Ala Leu Glu Glu Ala Arg Asn Val Pro Phe Gly Glu Glu Val Pro
        35                  40                  45

Glu Arg Leu Thr Leu Pro Glu Leu Gln Trp Met Leu Ser Asn Asn Glu
    50                  55                  60

Leu Thr Pro Val Gln Val Glu Glu Ala Pro Arg Ser Arg Leu Glu Leu
65                  70                  75                  80

Val Arg Arg Asp Asn Thr Val Thr Ser Lys Pro Leu Asn Cys Met Asn
                85                  90                  95

Tyr Phe Trp Lys Ser Arg Thr Ala Cys
            100                 105

<210> SEQ ID NO 37
<211> LENGTH: 125
<212> TYPE: PRT
<213> ORGANISM: Lophius americanus
```

-continued

```
<400> SEQUENCE: 37

Met Gln Cys Ile Arg Cys Pro Ala Ile Leu Ala Leu Leu Ala Leu Val
1               5                   10                  15

Leu Cys Gly Pro Ser Val Ser Ser Gln Leu Asp Arg Glu Gln Ser Asp
            20                  25                  30

Asn Gln Asp Leu Asp Leu Glu Leu Arg Gln His Trp Leu Leu Glu Arg
        35                  40                  45

Ala Arg Ser Ala Gly Leu Leu Ser Gln Glu Trp Ser Lys Arg Ala Val
    50                  55                  60

Glu Glu Leu Leu Ala Gln Met Ser Leu Pro Glu Ala Thr Phe Gln Arg
65                  70                  75                  80

Glu Ala Glu Asp Ala Ser Met Ala Thr Glu Gly Arg Met Asn Leu Glu
                85                  90                  95

Arg Ser Val Asp Ser Thr Asn Asn Leu Pro Pro Arg Glu Arg Lys Ala
            100                 105                 110

Gly Cys Lys Asn Phe Tyr Trp Lys Gly Phe Thr Ser Cys
        115                 120                 125

<210> SEQ ID NO 38
<211> LENGTH: 120
<212> TYPE: PRT
<213> ORGANISM: Carasius auratus

<400> SEQUENCE: 38

Met Arg Leu Cys Glu Leu His Cys Tyr Leu Ala Leu Leu Gly Leu Ser
1               5                   10                  15

Leu Val Leu Cys Gly Arg Cys Ala Asn Ser Gln Leu Glu Pro Asp Leu
            20                  25                  30

Asp Phe Arg His His Arg Leu Leu Gln Arg Ala Ser Ala Thr Gly Gln
        35                  40                  45

Ala Thr Gln Asp Phe Thr Lys Arg Asp Val Glu Lys Leu Leu Ser Leu
    50                  55                  60

Leu Ser Ile Pro Glu Met Glu Met Arg Glu Lys Gly Leu Ser Met Ala
65                  70                  75                  80

Gly Glu Ser Glu Asp Leu Arg Leu Glu Gln Glu Arg Ser Ala Glu Ser
                85                  90                  95

Ser Asn Gln Leu Pro Thr Arg Val Arg Lys Glu Gly Cys Lys Asn Phe
            100                 105                 110

Tyr Trp Lys Gly Phe Thr Ser Cys
        115                 120

<210> SEQ ID NO 39
<211> LENGTH: 111
<212> TYPE: PRT
<213> ORGANISM: Carasius auratus

<400> SEQUENCE: 39

Met Gln Leu Leu Ser Ser Leu Val Ser Leu Leu Val Leu Tyr Ser
1               5                   10                  15

Val Arg Ala Ala Ala Val Leu Pro Val Glu Glu Arg Asn Pro Ala Gln
            20                  25                  30

Ser Arg Glu Leu Ser Lys Glu Arg Lys Glu Leu Ile Leu Lys Leu Ile
        35                  40                  45

Ser Gly Leu Leu Asp Gly Val Asp Asn Ser Val Leu Asp Gly Glu Ile
    50                  55                  60

Ala Pro Val Pro Phe Asp Ala Glu Glu Pro Leu Glu Ser Arg Leu Glu
```

```
                65                  70                  75                  80
Glu Arg Ala Val Tyr Asn Arg Leu Ser Gln Leu Pro Gln Arg Asp Arg
                    85                  90                  95

Lys Ala Pro Cys Lys Asn Phe Phe Trp Lys Thr Phe Thr Ser Cys
                100                 105                 110

<210> SEQ ID NO 40
<211> LENGTH: 103
<212> TYPE: PRT
<213> ORGANISM: Rana ridibunda

<400> SEQUENCE: 40

Met Leu Gly Ser Ala Gly Thr Leu Leu Leu Leu Leu Ala Trp Gly
1               5                   10                  15

Ala Arg Ala Leu Ser Gln Pro Asp Asp Asn Arg Ile Thr Thr Gly Arg
                20                  25                  30

Asn Gln Asp Leu Asn Ala Ile Gln Gln Asp Leu Leu Leu Lys Leu Leu
            35                  40                  45

Ser Gly Trp Thr Asp Ser Arg Glu Ser Asn Leu Val Glu Val Glu Arg
        50                  55                  60

Asn Val Pro Asp Pro Pro Glu Pro Lys Ile Pro Pro Ser Val Lys Phe
65                  70                  75                  80

Pro Arg Leu Ser Leu Arg Glu Arg Lys Ala Pro Cys Lys Asn Phe Phe
                85                  90                  95

Trp Lys Thr Phe Thr Met Cys
                100

<210> SEQ ID NO 41
<211> LENGTH: 114
<212> TYPE: PRT
<213> ORGANISM: Ictalurus punctatus

<400> SEQUENCE: 41

Met Pro Ser Thr Arg Ile Gln Cys Ala Leu Ala Leu Ala Val Ala
1               5                   10                  15

Leu Ser Val Cys Ser Val Ser Gly Ala Pro Ser Asp Ala Lys Leu Arg
                20                  25                  30

Gln Phe Leu Gln Arg Ser Ile Leu Ala Pro Ser Val Lys Gln Glu Leu
            35                  40                  45

Thr Arg Tyr Thr Leu Ala Glu Leu Leu Ala Glu Leu Ala Glu Ala Glu
        50                  55                  60

Asn Glu Val Leu Asp Ser Asp Glu Val Ser Arg Ala Ala Glu Ser Glu
65                  70                  75                  80

Gly Ala Arg Leu Glu Met Glu Arg Ala Ala Gly Pro Met Leu Ala Pro
                85                  90                  95

Arg Glu Arg Lys Ala Gly Cys Lys Asn Phe Phe Trp Lys Thr Phe Thr
                100                 105                 110

Ser Cys

<210> SEQ ID NO 42
<211> LENGTH: 121
<212> TYPE: PRT
<213> ORGANISM: Lophius americanus

<400> SEQUENCE: 42

Met Lys Met Val Ser Ser Arg Leu Arg Cys Leu Leu Val Leu Leu
1               5                   10                  15
```

```
Leu Ser Leu Thr Ala Ser Ile Ser Cys Ser Phe Ala Gly Gln Arg Asp
            20                  25                  30

Ser Lys Leu Arg Leu Leu His Arg Tyr Pro Leu Gln Gly Ser Lys
        35                  40                  45

Gln Asp Met Thr Arg Ser Ala Leu Ala Glu Leu Leu Ser Asp Leu
    50                  55                  60

Leu Gln Gly Glu Asn Glu Ala Leu Glu Glu Asn Phe Pro Leu Ala
65                  70                  75                  80

Glu Gly Gly Pro Glu Asp Ala His Ala Asp Leu Glu Arg Ala Ala Ser
                85                  90                  95

Gly Gly Pro Leu Leu Ala Pro Arg Glu Arg Lys Ala Gly Cys Lys Asn
            100                 105                 110

Phe Phe Trp Lys Thr Phe Thr Ser Cys
            115                 120

<210> SEQ ID NO 43
<211> LENGTH: 114
<212> TYPE: PRT
<213> ORGANISM: Carasius auratus

<400> SEQUENCE: 43

Met Leu Ser Thr Arg Ile Gln Cys Ala Leu Ala Leu Leu Ser Leu Ala
1               5                   10                  15

Leu Ala Val Cys Ser Val Ser Ala Ala Pro Thr Asp Ala Lys Leu Arg
            20                  25                  30

Gln Leu Leu Gln Arg Ser Leu Leu Asn Pro Ala Gly Lys Gln Glu Leu
        35                  40                  45

Ala Arg Tyr Thr Leu Ala Asp Leu Leu Ser Glu Leu Val Gln Ala Glu
    50                  55                  60

Asn Glu Ala Leu Glu Pro Glu Asp Leu Ser Arg Ala Val Glu Lys Asp
65                  70                  75                  80

Glu Val Arg Leu Glu Leu Glu Arg Ala Ala Gly Pro Met Leu Ala Pro
                85                  90                  95

Arg Glu Arg Lys Ala Gly Cys Lys Asn Phe Phe Trp Lys Thr Phe Thr
            100                 105                 110

Ser Cys

<210> SEQ ID NO 44
<211> LENGTH: 115
<212> TYPE: PRT
<213> ORGANISM: Rana ridibunda

<400> SEQUENCE: 44

Met Gln Ser Cys Arg Val Gln Cys Ala Leu Thr Leu Leu Ser Leu Ala
1               5                   10                  15

Leu Ala Ile Asn Ser Ile Ser Ala Ala Pro Thr Asp Pro Arg Leu Arg
            20                  25                  30

Gln Phe Leu Gln Lys Ser Leu Ala Ser Ala Gly Lys Gln Glu Leu Ala
        35                  40                  45

Lys Tyr Phe Leu Ala Glu Leu Leu Ser Glu Pro Ser Gln Thr Asp Asn
    50                  55                  60

Glu Ala Leu Glu Ser Asp Asp Leu Pro Arg Gly Ala Glu Gln Asp Glu
65                  70                  75                  80

Val Arg Leu Glu Leu Glu Arg Ser Ala Asn Ser Ser Pro Ala Leu Ala
                85                  90                  95

Pro Arg Glu Arg Lys Ala Gly Cys Lys Asn Phe Phe Trp Lys Thr Phe
```

-continued

```
                        100                 105                 110

Thr Ser Cys
        115

<210> SEQ ID NO 45
<211> LENGTH: 116
<212> TYPE: PRT
<213> ORGANISM: Gallus gallus

<400> SEQUENCE: 45

Met Leu Ser Cys Arg Leu Gln Cys Ala Leu Ala Leu Leu Ser Ile Ala
1               5                   10                  15

Leu Ala Val Gly Thr Val Ser Ala Ala Pro Ser Asp Pro Arg Leu Arg
            20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Ser Gln Thr Glu
    50                  55                  60

Asn Glu Ala Leu Glu Ser Glu Asp Leu Ser Arg Gly Ala Glu Gln Asp
65                  70                  75                  80

Glu Val Arg Leu Glu Leu Glu Arg Ser Ala Asn Ser Asn Pro Ala Leu
                85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 46
<211> LENGTH: 116
<212> TYPE: PRT
<213> ORGANISM: Rattus norvegicus

<400> SEQUENCE: 46

Met Leu Ser Cys Arg Leu Gln Cys Ala Leu Ala Ala Leu Cys Ile Val
1               5                   10                  15

Leu Ala Leu Gly Gly Val Thr Gly Ala Pro Ser Asp Pro Arg Leu Arg
            20                  25                  30

Gln Phe Leu Gln Lys Ser Leu Ala Ala Ala Thr Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Pro Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 47
<211> LENGTH: 116
<212> TYPE: PRT
<213> ORGANISM: Bos taurus

<400> SEQUENCE: 47

Met Leu Ser Cys Arg Leu Gln Cys Ala Leu Ala Ala Leu Ser Ile Val
1               5                   10                  15
```

Leu Ala Leu Gly Gly Val Thr Gly Ala Pro Ser Asp Pro Arg Leu Arg
            20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Ile Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
                100                 105                 110

Phe Thr Ser Cys
        115

<210> SEQ ID NO 48
<211> LENGTH: 116
<212> TYPE: PRT
<213> ORGANISM: Macaca fascicularis

<400> SEQUENCE: 48

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
                100                 105                 110

Phe Thr Ser Cys
        115

<210> SEQ ID NO 49
<211> LENGTH: 116
<212> TYPE: PRT
<213> ORGANISM: Homo sapiens

<400> SEQUENCE: 49

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

```
Ala Pro Arg Glu Arg Lys Ala Gly Cys Lys Asn Phe Phe Trp Lys Thr
            100                 105                 110

Phe Thr Ser Cys
        115

<210> SEQ ID NO 50
<211> LENGTH: 47
<212> TYPE: DNA
<213> ORGANISM: Artificial Sequence
<220> FEATURE:
<223> OTHER INFORMATION: Primer

<400> SEQUENCE: 50
catgtacctt gatcaaccgt cacgtggcag ccagtagaag ttcttgc                47

<210> SEQ ID NO 51
<211> LENGTH: 29
<212> TYPE: DNA
<213> ORGANISM: Artificial Sequence
<220> FEATURE:
<223> OTHER INFORMATION: Primer

<400> SEQUENCE: 51
atttgcagcc aaggagccgc ctcgcagcc                                    29

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
catgtacctt gatcaaccgt ctcgtggcag                                   30
```

SOMATOSTATINS

This application claims the benefit of U.S. Provisional Application Ser. No. 60/168,934, filed Dec. 3, 1999, which is incorporated herein by reference in its entirety.

STATEMENT OF GOVERNMENT RIGHTS

This invention was made with government support under grants from the National Science Foundation, Grant No. OSR-9452892 and Grant No. IBN-9723058.

BACKGROUND OF THE INVENTION

Somatostatins are ubiquitous polypeptides known to affect basic biological processes such as growth, development, metabolism, and cell differentiation in vertebrates. Somatostatin was first isolated as a 14-amino acid peptide from ovine hypothalamus and found to inhibit the release of growth hormone from the pituitary gland (Brazeau et al., *Science*, 179, 77–79 (1973)). Since then somatostatins have been isolated from representatives of nearly every major group of vertebrates examined to date, from jawless fish to mammals (Conlon et al., *Regul Peptides*, 69, 95–103 (1997)). Somatostatins have been found broadly in the central (e.g., cerebral cortex, cerebellum, pineal, olfactory lobe, hypothalamus, spinal cord) and peripheral nervous systems, gastrointestinal tract (e.g. salivary glands, stomach, intestine), urogenital tract (e.g., bladder, prostate, collecting ducts of the kidney), pancreatic islets, adrenal glands, thyroid tissue, and placenta as well as in cerebral spinal fluid, blood, and saliva (Reichlin, "Somatostatin," *Brain peptide*, Krieger et al., eds., John Wiley and Sons, New York, pp. 711–752(1982); Gerich, "Somatostatin and analogues," *Diabetes mellitus: Theory and practice*, Ellenberg et al., eds., Medical Examinations, New York (1983); Wass, "Somatostatin," *Endocrinology*, DeGroot, ed., W B Saunders, Philadelphia, Pa. (1989); Patel, "General aspects of the biology and function of somatostatin," *Basic and clinical aspects of neuroscience*, Weil et al., eds., Springer-Verlag, Berlin (1992)). In neurons and cells, somatostatins are often co-localized with other factors (e.g., norepinephrine, CCK, neuropeptide-Y, CGRP, GABA, VIP, substance P) (Gibbins, "Co-existence and co-function," *The comparative physiology of regulatory peptides*, Holmgren, ed., Chapman and Hall, London/New York (1989)).

Somatostatins also possess a vast diversity of physiological actions. In addition to secretotropic effects (including the effect on growth hormone secretion for which the family was named), somatostatins have been reported to have neurotropic and myotropic effects as wells as effects on transport, metabolism, growth, differentiation, and modulation of functional development. It should be noted that there is overlap between and among these somewhat arbitrary classes of action. For example, the inhibition of growth hormone secretion clearly affects growth and the inhibition of insulin secretion clearly affects metabolism. At the same time, the inhibition of growth hormone also impacts metabolism while the inhibition of insulin has ramifications on growth (Norman and Litwack, *Hormones*, Academic Press, New York (1997)). In addition to such actions which result in physiological "cross talk," somatostatins also have direct effects on the various classes of action. For example, somatostatins have been shown to affect growth (e.g., proliferation) and intermediary metabolism (e.g., lipolysis) directly in target cells (Patel, "General aspects of the biology and function of somatostatin," *Basic and Clinical Aspects of Neuroscience*, Weil et al., eds., Springer-Verlag, Berlin (1992); Sheridan, *Comp. Biochem. Physiol.*, 107b, 495–508 (1994)). Considering these various roles, somatostatins may be of considerable importance in various diseases including neuroendocrine tumors, diabetes mellitus, epilepsy, Alzheimer and Huntington Diseases, and AIDS (Lamberts et al., *Endocrine Rev.*, 12, 450–482 (1991); Patel et al., *Life Sci.*, 57, 1249–1265 (1995)).

Most somatostatins appear to be synthesized as a long chain prepropeptide, which can be subsequently processed to yield a propeptide (typically ranging in size from 25–28 amino acids) and, in some cases, further processed to yield a peptide of about 14 amino acids. This differential processing introduces considerable molecular heterogeneity into somatostatins. It is believed that in mammals, differential processing of the transcription product of a single gene may account for the tissue-, organ- and cell-specific activities of various somatostatins. The bioactivity of secreted somatostatins is mediated by cell-surface somatostatin receptors which likely differentiate among the various forms of somatostatin present in an organism. The molecular heterogeneity of somatostatins appears to be even greater in some non-mammalian organisms. Fish and some other non-mammals, for example, may possess several somatostatin genes, each of which may be differentially processed.

Notwithstanding the heterogeneity that characterizes the longer chain preprosomatostatins and prosomatostatins, the somatostatin tetradecapeptide SS-14 (Ala-Gly-Cys-Lys-Asn-Phe-Phe-Trp-Lys-Thr-Phe-Thr-Ser-Cys; SEQ ID NO:1), present at the C-terminus of the longer forms, is completely conserved among such mammals as monkeys, rats, cows, sheep, chickens and humans. Somatostatins found in both mammals and non-mammals typically contain the C-terminal SS-14 sequence (SEQ ID NO:1). Non-mammals, however, frequently express additional somatostatins that contain variant C-terminal tetradecapeptides with substitutions at one or more sites, such as [Tyr$^7$, Gly$^{10}$]-SS-14 (SEQ ID NO:2). This alternative somatostatin peptide has modifications at positions 7 and 10 when compared to the mammalian sequence [Phe$^7$, Thr$^{10}$]. Somatostatins that contain the "mammalian"-type 14-mer sequence (SEQ ID NO:1) at the C-terminus are considered to be part of the "SS-I" family, whereas those that contain a 14-mer sequence having the [Tyr$^7$, Gly$^{10}$] modification (SEQ ID NO:2) are considered to be part of the "SS-II" family.

In mammalian systems, somatostatin is secreted into the blood and is vascularly active. Different cells can synthesize different versions of the polypeptide. Secreted somatostatin is also known to have a local paracrine activity. There are a number of human diseases (e.g., growth disorder, diabetes, and several neurological disorders) that may be treated with somatostatin analogs. Also, some conditions (e.g., tumors) result from overproduction of somatostatin, and there is no known somatostatin antagonist for treatment of such disorders. New somatostatin analogs (both agonists and antagonists) that have the potential to treat these and other human diseases would be a welcome addition to current therapeutic strategies.

SUMMARY OF THE INVENTION

The invention provides novel somatostatin polypeptides that contain amino acid sequences found in *Oncorhynchus mykiss* preprosomatostatin I (PPSS-I; SEQ ID NO:3) and/or *Oncorhynchus mykiss* preprosomatostatin II" (PPSS-II"; SEQ ID NO:15). Also provided are bioactive analogs and subunits of the somatostatin polypeptides of the invention. Preferred somatostatin polypeptides include polypeptides having at least one amino acid sequence selected from the group consisting of SEQ ID NOS:1, 2, 3, 4, 5, 6, 7, 9, 10, 11, 12, 13, 15, 16, 17, 18, and 19, and bioactive analogs and subunits thereof.

Polynucleotides encoding somatostatin polypeptides of the invention and/or bioactive analogs and subunits thereof, as well as those that are substantially complementary thereto, are also provided.

The invention further provides a method for identifying a modified somatostatin polypeptide. The amino acid sequence of a somatostation polypeptide of the invention is aligned with the amino acid sequence of a reference somatostatin polypeptide, preferably a mammalian somatostatin polypeptide, and at least one site or region of differing amino acid sequence is identified. Either the somatostatin polypeptide of the invention or the reference somatostatin polypeptide is then modified to incorporate at least one amino acid substitution, insertion, or deletion from the analogous site or region in the other somatostatin polypeptide to yield the amino acid sequence of a modified somatostatin polypeptide. Optionally, the method further includes synthesizing the modified somatostatin polypeptide and assaying the modified somatostatin polypeptide for biological activity. Biological activity is preferably determined by determining whether the modified somatostatin polypeptide binds to a human somatostatin receptor molecule or inhibits the binding of a natural ligand of the human somatostatin receptor molecule. Preferably, the modified somatostatin polypeptide identified according to the method of the invention is a somatostatin agonist or antagonist.

Also provided by the invention is a fusion polypeptide, wherein an N-terminal somatostatin region is fused (i.e., covalently linked) to a selected C-terminal region. The N-terminal somatostatin region includes one or more first amino acid sequences that contain an isoform or isoform fragment of PPSS-I and/or PPSS-II" as described herein, or portion thereof. The C-terminal region contains a second amino acid sequence that preferably encodes a bioactive peptide moiety.

BRIEF DESCRIPTION OF THE FIGURES

FIG. 1 schematically represents the proposed biosynthesis of somatostatins from multiple somatostatin genes in rainbow trout; arrows denote putative cleavage sites. Processing details are set forth in the legends to FIG. 2 and FIG. 3.

FIG. 2 shows the nucleotide sequence (SEQ ID NO:8) and the deduced amino acid sequence (SEQ ID NO:3) of the PPSS-I cDNA obtained from the endocrine pancreas of rainbow trout. The putative N-terminal signal sequence (amino acids −100 through −77; SEQ ID NO:7) is overlined. The presumptive coding region for somatostatin SS-14 peptide (SEQ ID NO:1, wherein the N-terminal Ala is denoted by a double arrow) is preceded by a putative Arg-Lys dibasic cleavage site. An N-terminally extended 26-amino acid prosomatostatin product (amino acids −12 through +14; SEQ ID NO:4; wherein the N-terminal Ala is denoted by a single arrow) includes the SS-14 sequence (SEQ ID NO:1) and is preceded by an Arg monobasic cleavage site. The 26 amino acid proprotein (SEQ ID NO:4) contains a 12 amino acid N-terminal extension sequence (amino acids −12 through −1; SEQ ID NO:6) linked to SS-14 (SEQ ID NO:1). The 114 amino acid preproprotein (SEQ ID NO:3) contains an 88 amino acid N-terminal extension sequence (amino acids −100 through −13; SEQ ID NO:5) linked to the 26 amino acid proprotein sequence (SEQ ID NO:4). The translation stop codon stop sequence is denoted by asterisks, and the putative polyadenylation signal is underlined.

FIG. 3 shows the nucleotide sequences (SEQ ID NO:14 and SEQ ID NO:20) and the deduced amino acid sequence (SEQ ID NO:9 and SEQ ID NO:15) of the PPSS-II' cDNA and PPSS-II" cDNA, respectively, obtained from the endocrine pancreas of rainbow trout. Nucleotides and amino acids are numbered in right margin, and gaps are denoted with asterisks for maximum alignment. The amino acids are shown for PPSS-II". For PPSS-II', only the amino acids that differ from those in PPSS-II" are shown, but it should be understood that where no amino acid is shown, it is the same as the amino acid at the analogous site on PPSS-II". The putative N-terminal signal sequence (PPSS-II': amino acids −101 through −77, SEQ ID NO:13; PPSS-II": amino acids −97 through −73, SEQ ID NO:19) is underlined. The presumptive coding region for SS-14 (SEQ ID NO:2, wherein the N-terminal Ala is denoted by a single arrow) is preceded by a putative Arg-Lys dibasic cleavage site denoted by open circles and contains [$Tyr^7$, $Gly^{10}$] substitutions characteristic of the PPSS-II family. An N-terminally extended prosomatostatin product (PPSS-II': 28 amino acids, amino acids −14 through +14, SEQ ID NO:10; PPSS-II": 25 amino acids, amino acids −11 through +14, SEQ ID NO:16; wherein the N-terminal Ser is denoted by a double arrow) includes the [$Tyr^7$, $Gly^{10}$]SS-14 sequence (SEQ ID NO:2) and is preceded by an Arg monobasic cleavage site. The 28 amino acid PPSS-II' proprotein (SEQ ID NO:10) contains a 14 amino acid N-terminal extension sequence (amino acids −14 through −1; SEQ ID NO:12) linked to [$Tyr^7$, $Gly^{10}$]SS-14 (SEQ ID NO:2). The 25 amino acid PPSS-II" proprotein (SEQ ID NO:16) contains an 11 amino acid N-terminal extension sequence (amino acids −11 through −1; SEQ ID NO:18) linked to [$Tyr^7$, $Gly^{10}$]SS-14 (SEQ ID NO:2). The 115 amino acid PPSS-II' preproprotein (SEQ ID NO:9) contains an 87 amino acid N-terminal extension sequence (amino acids −101 through −14; SEQ ID NO:11) linked to the 28 amino acid PPSS-II' proprotein sequence (SEQ ID NO: 10). The 111 amino acid PPSS-II" preproprotein (SEQ ID NO:15) contains an 86 amino acid N-terminal extension sequence (amino acids −97 through −11; SEQ ID NO:17) linked to the 25 amino acid PPSS-II" proprotein sequence (SEQ ID NO: 16).

FIG. 4 diagrams the sequence strategy used for 5' and 3' rapid amplification of cDNA ends (RACE).

FIG. 5 compares the amino acid (lower left) and cDNA nucleotide (upper right) sequence identities vertebrate somatostatins. AF I denotes anglerfish (Hobart et al., *Nature,* 288, 137–141 (1980)), CF I denotes catfish I (Minth et al., *J. Biol. Chem.* 257, 10372–10377 (1982)), H denotes human (Shen et al., *Proc. Natl. Acad. Sci. USA,* 79, 4575–4579 (1982)), B denotes bovine (Su et al., *Mol. Endocrinol.,* 2, 209–216 (1988)), M denotes monkey (Travis and Sutcliffe, *Proc. Natl. Acad. Sci. USA,* 85, 1696–1700(1988)), R denotes rat (Goodman et al., *J. Biol. Chem.,* 258, 5570–5573 (1983)), C denotes chicken (Nata, *GenBank direct submission,* Accession No. X60191 (1991)), FR I denotes frog (Tostivint et al., *Proc. Natl. Acad. Sci. USA,* 93, 12605–12610 (1996)), TR II' denotes rainbow trout-II' (Moore et al., *Gen. Comp. Endocrinol.,* 98, 253–261 (1995)), TR II" denotes rainbow trout-II", and TR I denotes rainbow trout-I.

FIG. 6 aligns the deduced rainbow trout PPSS-I C-terminal region amino acid sequence to other PPSS-I C-terminal region amino acid sequences from other vertebrates. [a]Sequences arranged for maximum alignment; identity is greatest if it is assumed there has been a 2-amino acid deletion (designated by asterisks) from rainbow trout and bowfin (Wang et al., *Regul Peptides,* 47, 33–39 (1993). [b]Putative peptide deduced from cDNA. [c]Peptide sequence deduced from cDNA and confirmed by processing analysis for anglerfish I (Hobart et al., *Nature*, 288, 137–141 (1980); Goodman et al., *Proc. Natl. Acad. Sci. USA*, 77, 5869–5873 (1980); Andrews and Dixon, *Biochemistry* 26, 4853–4861 (1987)), catfish I (Andrews and Dixon, *J. Biol. Chem.*, 256, 8267–8270 (1981); Minth et al., *J. Biol. Chem.*, 257, 10372–10377 (1982)); and frog (Vaudry et at., *Biochem. Biophys. Res. Commun.*, 188, 477–482 (1992); Tostivint et al., *Proc. Natl. Acad. Sci. USA*, 93, 12605–12610 (1996)).
[d]Peptide sequence derived directly from analysis of isolates of islet extracts obtained from hagfish (Conlon et at., *Endocrinology*, 122, 1855–1859 (1988)), lamprey (Andrews et al., *J. Biol. Chem.*, 263, 15809–15814(1988)), torpedo (Conlon et al., *Gen. Comp Endocrinol.*, 60, 406–413 (1985)), ratfish (Conlon et al., *Gen. Comp. Endocrinol.*, 80, 314–320 (1990)), sturgeon (Nishii et al., *Gen. Comp. Endocrinol.*, 99, 6–12 (1995)), eel (Conlon et al., *Endocrinology*, 122, 1855–1859 (1988)), flounder and sculpin (Conlon et al., *Eur. J. Biochem.*, 168, 647–652 (1987a)), salmon (Plisetskaya et al., *Gen. Comp. Endocrinol.*, 63, 252–263 (1986)), salamander (Cavanaugh et al., *Gen. Comp. Endocrinol.*, 101, 12–20 (1996)), pigeon (Spiess et al., *Proc. Natl. Acad. Sci. USA* 76, 2974–2978 (1979)), alligator (Wang and Conlon, *Peptides*, 14, 573–579 (1993)), and ovine (28-amino acid form shown for purposes of comparison; Pradayrol et al., *FEBS Lett.*, 109, 55–58 (1980)).

FIG. 7 aligns the deduced rainbow trout PPSS-I, PPSS-II' and PPSS-II" amino acid sequences with PPSSs of other vertebrates; sequence identity was maximized by inserting gaps (denoted by dashed lines); conserved amino acids are shaded. H denotes human (Shea et al., *Proc. Natl. Acad. Sci. USA* 79, 4575–4579 (1982)); M denotes monkey (Travis and Sutcliffe, *Proc. Natl. Acad. Sci. USA,* 85, 1696–1700 (1988)); B denotes bovine (Su et al., *Mol. Endocrinol,* 2, 209–216 (1988)); R denotes rat (Goodman et al., *J. Biol. Chem.*, 258, 570–573 (1983)); C denotes chicken (Nata, *GenBank direct submission,* Accession No. X60191 (1991)); FR I and FR II denote frog I and frog II (Tostivint et al., *Proc. Natl. Acad. Sci. USA* 93, 12605–12610 (1996)); AF I denotes anglerfish I (Hobart et al., *Nature,* 288, 137–141 (1980)); AF II denotes anglerfish II (Goodman et at., *Proc. Natl. Acad. Sci. USA,* 77, 5869–5873 (1980); Goodman et al., *Proc. Natl. Acad. Sci. USA.* 79, 1682 (1982); Hobart et al., *Nature,* 288, 137–141 (1980)); CF I denotes catfish I (Minth et al., *J. Biol. Chem.*, 257, 10372–10377(1982)); CF II denotes caffish II (Fujita et al., *Peptides,* 2, 123–131 (1981)); GF I-III deonates goldfish I-III (Lin et al., *Endocrinology,* 140, 2089–2099 (1999)); TRI denotes trout I; TRII' denotes trot II' (Moore et at., *Gen. Comp. Endocrinol.*, 98, 253–261 (1995)); and TRII" denotes trout II".

Figure 8:
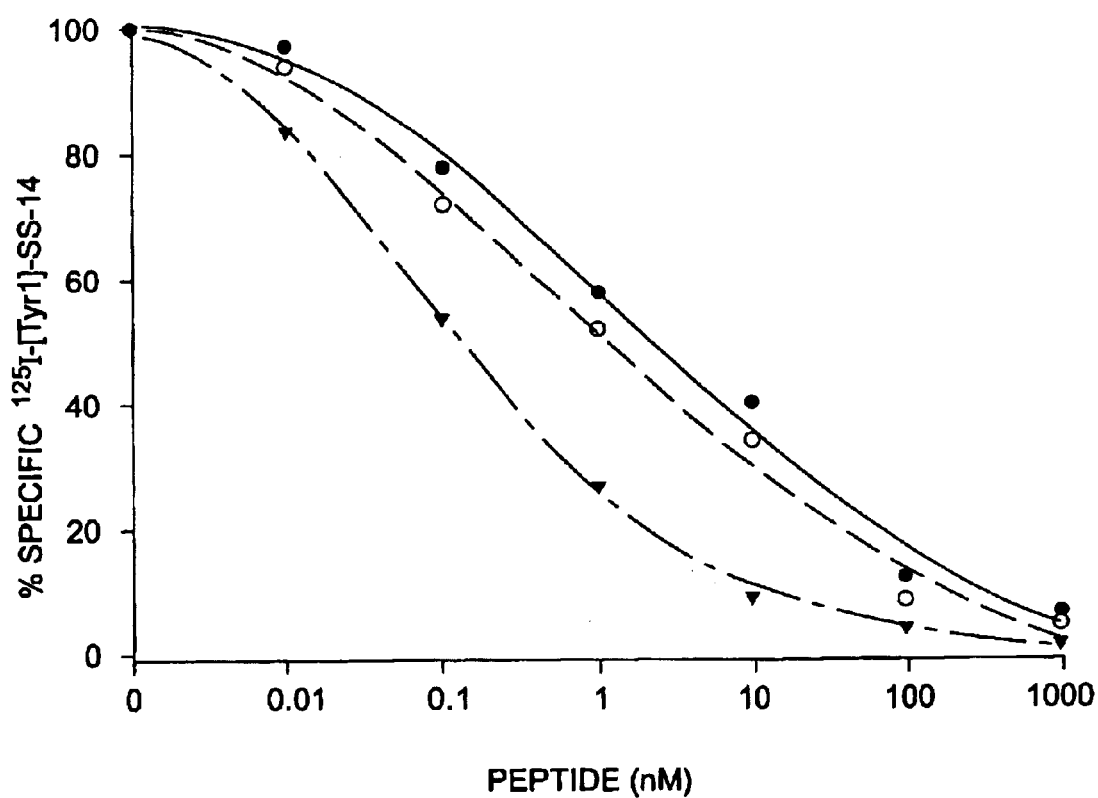

FIG. 8 graphically shows the ability of synthetic salmonid SS-25 (filled inverted triangles) mammalian SS-14 (filled circles) and mammalian SS-28 (open circles) to inhibit the binding of $I^{125}$-[Tyr1]-SS-14 to microsomes prepared from COS-7 cells transiently expressing the human SS type 1 receptor.

DETAILED DESCRIPTION OF THE PREFERRED EMBODIMENTS

In one aspect, the present invention provides a novel somatostatin polypeptide or biologically active analog, subunit or derivative thereof. A polynucleotide that encodes a novel somatostatin polypeptide or biologically active analog, subunit or derivative thereof is also provided. As used herein, the term "polypeptide" refers to a polymer of two or more amino acids joined together by peptide bonds. The terms peptide, oligopeptide, and protein are all included within the definition of polypeptide. In particular, the term "somatostatin polypeptide" includes somatostatin precursor polypeptides (e.g., somatostatin prepropeptides, which are typically over 100 amino acids in length), as well as shorter polypeptides (e.g., somatostatin propeptides, typically about 25–28 amino acid in length, and somatostatin peptides, typically about 14 amino acids in length). A "biologically active" somatostatin analog or subunit is a polypeptide that is able to bind to a somatostatin receptor molecule, preferably a human somatostatin receptor molecule. A method for evaluating binding activity is described, for example, in Example V herein.

A biologically active "analog" of a somatostatin polypeptide includes a somatostatin polypeptide that has been modified by the addition, substitution, or deletion of one or more amino acids, or that has been chemically or enzymatically modified, e.g., by attachment of a reporter group, by an N-terminal, C-terminal or other functional group modification or derivatization, or by cyclization, as long as the analog retains biological activity. Amino acid substitutions are preferably conserved amino acid substitutions, such as substitutions between negatively charged residues (glutamate and aspartate), between positively charge residues (lysine, histidine and arginine), among nonpolar residues (valine, alanine, leucine, isoleucine and phenylalanine), or between polar residues (serine and threonine).

A biologically active "subunit" of a somatostatin polypeptide includes a somatostatin polypeptide that has been truncated at either the N-terminus, or the C-terminus, or both, by one or more amino acids, as long as the truncated polypeptide retains bioactivity and contains at least 7 amino acids, more preferably at least 10 amino acids, most preferably at least 12 amino acids.

With respect to a somatostatin polypeptide comprising the 14 amino acid sequence SS-14 (SEQ ID NO:1) or [Tyr$^7$, Gly$^{10}$]-SS-14 (SEQ ID NO:2), a preferred biologically active analog or subunit of such somatostatin polypeptide does not contain any amino acid substitutions, deletions or additions at positions 6–11 of that 14 amino acid sequence, as those positions are very important for binding to a somatostatin receptor, but may contain substitutions, deletions, or additions at other sites. Preferred substitutions include proline at position +2 and serine at position +5. Examples of biologically active analogs of SS-14 from PPSS-I have been described in Reisine et al. (*Endocr. Rev.* 16:427–442 (1995)) and include amino acid-deleted or amino acid-substituted compounds, dicarba analogs, bicylclic octapeptide analogs (e.g., SMS201-995A, sometimes known as octreotide or by the tradename SANDOSTATIN) and cyclic hexapeptides (e.g., MK687).

A preferred polypeptide and/or polynucleotide of the invention is one that is derived from rainbow trout (*Oncorhynchus mykiss*). The use of the term "derived from" is not intended to limit the invention to a polypeptide or polynucleotide that is physically isolated from rainbow trout, but is meant to include biologically active somatostatin biomolecules having all or a portion of a trout somatostatin amino acid or nucleotide sequence, whether isolated from trout or synthesized chemically, enzymatically, or using genetic engineering.

Figure 1:
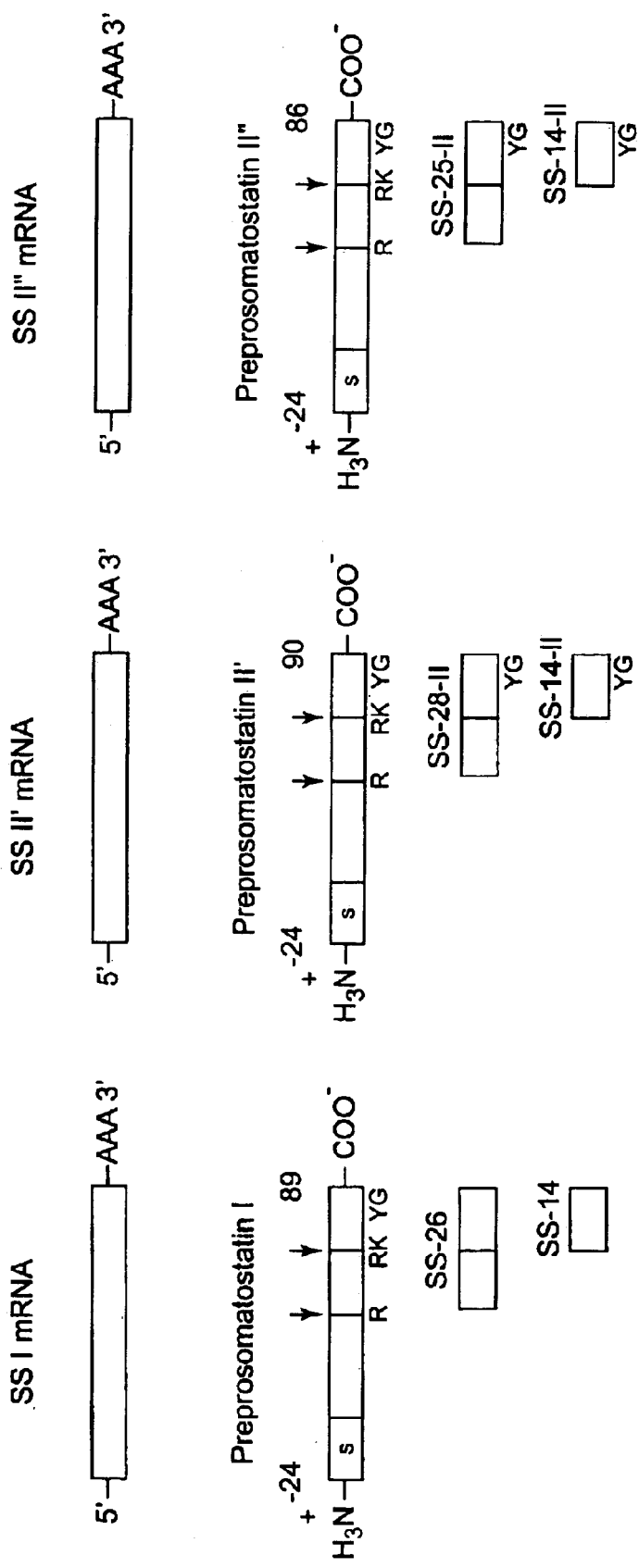

Trout preprosomatostatin-I (PPSS-I) is described herein in Example I and is shown in FIG. 1 and FIG. 2. PPSS-I characterized by a 745 base pair cDNA (SEQ ID NO:8) that encodes a precursor protein of about 114 amino acids (SEQ ID NO:3) that appears capable of being processed into a 26 amino acid polypeptide (SEQ ID NO:4), and further into a 14 amino acid peptide (SS-14)(SEQ ID NO:1). Because this tetradecapeptide (SEQ ID NO:1) has the "mammalian"-type sequence, these somatostatins are members of the SS-I family.

Trout preprosomatostatin-II' (PPSS-II') was reported by Moore et al. (*Gen. Comp. Endocrinol.* 98:253–261 (1995)), and is shown in FIG. 1 and FIG. 3. PPSS-II' is characterized by a 624 base pair cDNA (SEQ ID NO:14) that encodes a precursor protein of about 115 amino acids (SEQ ID NO:9) that appears capable of being processed into a 28 amino acid polypeptide (SEQ ID NO:10), and further into a 14 amino acid peptide (SEQ ID NO:2). Because this tetradecapeptide has the modified [$Tyr^7$, $Gly^{10}$] sequence, these somatostatins are members of the SS-II family.

Trout preprosomatostatin-II" (PPSS-II") is described herein in Example III and is shown in FIG. 1 and FIG. 3. PPSS-II" is charactedzed by a 600 base pair cDNA (SEQ ID NO:20) that encodes a precursor protein of about 111 amino acids (SEQ ID NO: 15) that appears capable of being processed into a 25 amino acid polypeptide (SEQ ID NO:16), and further into a 14 amino acid peptide (SEQ ID NO:2). Because this tetradecapeptide has the modified [$Tyr^7$, $Gly^{10}$] sequence, these somatostatins are members of the SS-II family.

Preferred somatostatin polypeptides of the invention include the different "isoforms" of PPSS-I and PPSS-II" derived from trout, as well as "isoform fragments" that result from actual or putative N-terminal processing of such isoforms. Preferred PPSS-I polypeptides thus include preprosomatostatin I (114 amino acid isoform) (SEQ ID NO:3); the N-terminal pre-sequence of PPSS-I (88 amino acid isoform fragment) (SEQ ID NO:5); prosomatostatin 1 (26 amino acid isoform) (SEQ ID NO:4); and the N-terminal pro-sequence of PPSS-I (12 amino acid isoform fragment) (SEQ ID NO:6) Preferred PPSS-II" polypeptides thus include preprosomatostatin II" (111 amino acid isoform) (SEQ ID NO:15); the N-terminal pre-sequence of PPSS-II" (86 amino acid isoform fragment) (SEQ ID NO:17); prosomatostatin II" (25 amino acid isoform) (SEQ ID NO:16); and the N-terminal pro-sequence of PPSS-II" (11 amino acid isoform fragment) (SEQ ID NO:18)

Also preferred are polypeptides that include all or a portion of one or more PPSS-I and/or PPSS-II" amino acid sequences derived from trout. If only a portion of a PPSS-I and/or PPSS-II" sequence is included in the polypeptide, the portion so included contains at least 7, and preferably at least 10, more preferably at least 12, contiguous amino acids of a PPSS-I and/or PPSS-II" sequence. Furthermore, if the included portion of the PPSS-I and/or PPSS-II" sequence contains all or a portion of the C-terminal 14-mer SEQ ID NO:1, the C-terminal 14-mer SEQ ID NO:2, or the C-terminal 25-mer SEQ ID NO:16, then said included portion also includes at least an additional 7, and preferably an additional 10, more preferably at least 12 contiguous amino acids of a PPSS-I and/or PPSS-II" sequence. The additional contiguous amino acids need not be, but may be, contiguous to the included portion of the C-terminal 14-mer. An example of a polypeptide that includes all or a portion of a PPSS-I and/or PPSS-II" sequence is a chimeric polypeptide that contains the prosomatostatin sequence of human somatostatin (SEQ ID NO:21) and the presequence of PPSS-I derived from trout (SEQ ID NO:5).

Preferred biologically active analogs of PPSS-I and/or PPSS-II" sequences derived from trout include (1) analogs of PPSS-I and/or PPSS-II" isoform sequences that are at least 85% identical, more preferably at least 90% identical, most preferably at least 95% identical to PPSS-I and PPSS-II" isoform sequences SEQ ID NOs:3, 4, 15 or 16; and (2) analogs of PPSS-I and/or PPSS-II" isoform fragment sequences that are at least 90% identical, more preferably at least 95% identical to PPSS-I and PPSS-II" isoform fragment sequences SEQ ID NOs:3, 4, 15 or 16. Such analogs contain one or more amino acid deletions, insertions, and/or substitutions relative to the reference PPSS-I and/or PPSS-II" sequence, and may further include chemical and/or enzymatic modifications and/or derivatizations as described above.

Percent identity is determined by aligning the residues of the two amino acid or nucleotide sequences to optimize the number of identical amino acids or nucleotides along the lengths of their sequences; gaps in either or both sequences are permitted in making the alignment in order to optimize the number of identical amino acids or nucleotides, although the amino acids or nucleotides in each sequence must nonetheless remain in their proper order. Preferably, two amino acid sequences are compared using the Blastp program, version 2.0.9, of the BLAST 2 search algorithm as described by Tatusova, et al. (*FEMS Microbiol. Lett.,* 174 247–250 (1999)) and available on the world wide web at www.ncbi.nlm.nih.gov/blast.html. Preferably, the default values for all BLAST 2 search parameters are used including matrix=BLOSUM62; open gap penalty=11, extension gap penalty=1, gapx_dropoff=50, expect=10, wordsize=3, and filter on. Likewise, two nucleotide sequences are compared using the Blastn program, version 2.0.11, of the BLAST 2 search algorithm, also as described by Tatusova, et al. (*FEMS Microbiol Lett,* 174, 247–250(1999)) and available on the world wide web at www.ncbi.nlm.nih.gov/blast.html. Preferably, the default values for all BLAST 2 search parameters are used, including reward for match=1, penalty for mismatch=−2, open gap penalty=5, extension gap penalty=2, gapx_dropoff=50, expect=10, wordsize=11, and filter on.

It should be understood that a polynucleotide that encodes a novel somatostatin polypeptide derived from *Oncorhynchus mykiss* according to the invention is not limited to a naturally occurring polynucleotide derived from *Oncorhynchus mykiss*, such as a polynucleotide that includes all or a portion of a PPSS-I and/or PPSS-II" genomic or cDNA nucleotide sequence, but also includes the class of polynucleotides that encode such polypeptides as a result of the degeneracy of the genetic code. For example, the naturally occurring nucleotide sequence SEQ ID NO:8 is but one member of the class of nucleotide sequences that encodes a polypeptide having amino acid SEQ ID NO:3. This class of nucleotide sequences that encode a selected polypeptide sequence is large but finite, and the nucleotide sequence of each member of the class can be readily determined by one skilled in the art by reference to the standard genetic code, wherein different nucleotide triplets are known to encode the same amino acid. Likewise, a polynucleotide of the invention that encodes a biologically active analog or subunit of a somatostatin polypeptide includes the multiple members of the class of polynucleotides that encode the selected polypeptide sequence.

Moreover, a polynucleotide that "encodes" a polypeptide of the invention optionally includes both coding and non-coding regions, and it should therefore be understood that, unless expressly stated to the contrary, a polynucleotide that "encodes" a polypeptide is not structurally limited to nucleotide sequences that encode a polypeptide but can include other nucleotide sequences outside (i.e., 5' or 3' to) the coding region.

The polynucleotides of the invention can be DNA, RNA, or a combination thereof, and can include any combination of naturally occurring, chemically modified or enzymatically modified nucleotides. As noted above, the polynucleotide can be equivalent to the polynucleotide fragment encoding a somatostatin polypeptide, or it can include said polynucleotide fragment in addition to one or more additional nucleotides. For example, the polynucleotide of the invention can be a vector, such as an expression or cloning vector. A vector useful in the present invention can be circular or linear, single-stranded or double-stranded, and can include DNA, RNA, or any modification or combination thereof. The vector can be a plasmid, a cosmid, or a viral vector, such as baculovirus. Preferably, the polynucleotide of the invention takes the form of an expression vector that is capable of expression in an organism or in a cell of an organism, in culture or in vivo. An organism or cell in which the coding sequence of the vector can be expressed can be a vertebrate, and preferably a veterinary mammal or a human. Preferably, the vector is expressible in bacterial expression system, such as E. coli, yeast, mammalian cell culture or insect cells.

It should be understood that the polynucleotide of the invention can be single-stranded or double-stranded, and further that a single-stranded polynucleotide of the invention includes a polynucleotide fragment having a nucleotide sequence that is complementary to the nucleotide sequence of the single-stranded polynucleotide. As used herein, the term "complementary" refers to the ability of two single-stranded polynucleotide fragments to base pair with each other, in which an adenine on one polynucleotide fragment will base pair with a thymidine (or uracil, in the case of RNA) on the other, and a cytidine on one fragment will base pair with a guanine on the other. Two polynucleotide fragments are complementary to each other when a nucleotide sequence in one polynucleotide fragment can base pair with a nucleotide sequence in a second polynucleotide fragment. For instance, 5'-ATGC and 5'-GCAT are fully complementary, as are 5'-GCTA and 5'-TAGC.

Further, the single-stranded polynucleotide of the invention also includes a polynucleotide fragment having a nucleotide sequence that is substantially complementary to (a) a nucleotide sequence that encodes a novel somatostatin polypeptide according to the invention, or (b) the complement of such nucleotide sequence. "Substantially complementary" polynucleotide fragments can include at least one base pair mismatch, such that at least one nucleotide present on a second polynucleotide fragment, however the two polynucleotide fragments will still have the capacity to hybridize. For instance, the middle nucleotide of each of the two DNA fragments 5'-AGCAAATAT and 5'-ATATATGCT will not base pair, but these two polynucleotide fragments are nonetheless substantially complementary as defined herein. Two polynucleotide fragments are substantially complementary if they hybridize under hybridization conditions exemplified by 2×SSC (SSC: 150 mM NaCl, 15 mM trisodium citrate, pH 7.6) at 55° C. Substantially complementary polynucleotide fragments for purposes of the present invention preferably share at least one region of at least 20 nucleotides in length which shared region has at least 60% nucleotide identity, preferably at least 80% nucleotide identity, more preferably at least 90% nucleotide identity and most preferably at least 95% nucleotide identity. Particularly preferred substantially complementary polynucleotide fragments share a plurality of such regions. Locations and levels of nucleotide sequence identity between two nucleotide sequences can be readily determined using CLUSTALW multiple sequence alignment software (J. Thompson et al., *Nucleic Acids Res.*, 22:4673–4680 (1994)) available on the world wide web at www.ebi.ac.uk/clustalw/.

In another aspect, the invention provides methods of making the novel somatostatin polypeptides of the invention, as well as methods of making the multiple polynucleotides that encode them. The methods include biological, enzymatic, and chemical methods, as well as combinations thereof, and are well-known in the art. For example, a somatostatin polypeptide can be expressed in a host cell from using standard recombinant DNA technologies; it can be enzymatically synthesized in vitro using a cell-free RNA based system; or it can be synthesized using chemical technologies such as solid phase peptide synthesis, as is well-known in the art.

In yet another aspect, the invention provide a method for identifying novel polypeptides that have somatostatin activity. This method is based on comparative analysis of (a) a somatostatin amino acid sequence derived from trout PPSS-I or PPSS-II", preferably an amino acid sequence of at least one isoform of PPSS-I (SEQ ID NO:3, 4, or 1) or PPSS-II" (SEQ ID NO:15, 16 or 2) or isoform fragment of PPSS-I (SEQ ID NO:5 or 6) or PPSS-II" (SEQ ID NO:17 or 18) and (b) the amino acid sequence of an analogous region of a somatostatin polypeptide of another organism, preferably a mammal, more preferably a human. The reference somatostatin polypeptide can be either the trout polypeptide or the polypeptide from the other organism. The sequences are aligned, and sites having different amino acids are identified. Then, a novel candidate somatostatin sequence is postulated that is represented by the reference polypeptide modified to contain one or more amino acid substitutions, modifications, a deletions as suggested by the other polypeptide to which it is compared. The candidate somatostatin polypeptide is synthesized, assayed for somatostatin activity (i.e., binding to a somatostatin receptor of interest), and, optionally, further assayed for any desired therapeutic effect.

Using this method, novel somatostatin polypeptides can be identified that function as either agonists or antagonist of the reference polypeptide or other naturally occurring somatostatin, or that have altered binding specificity or selectivity when compared to the reference polypeptide or other naturally occurring somatostatin. For example, binding of longer somatostatin isoforms to receptor molecules is likely affected by the amino acid sequence of the N-terminal region (e.g., the region upstream from the C-terminal 14 amino acid peptide). All or a portion of an N-terminal trout somatostatin amino acid sequence according to the invention can, for example, be fused to the C-terminal portion of another somatostatin or somatostatin analog in order to target the analog or affect binding of the analog or modulate the binding activity of the analog. For example, a novel somatostatin that contains a trout PPSS-II" presequence (SEQ ID NO:17) joined to the mammalian SS-28 prosomatostatin sequence (SEQ ID NO:21) can be postulated and evaluated for somatostatin activity according to the method. Likewise, a small scale substitution of the alternative SS-14 residues Tyr$^7$ and Gly$^{10}$ into the C-terminus of trout PPSS-I which contains the Phe$^7$ and Thr$^{10}$ (SEQ ID NO:2) yields a novel somatostatin polypeptide that can also be evaluated according to the method of the invention.

Advantageously, the method of the invention can be used to identify novel somatostatin polypeptides that will bind to the human somatostatin receptor and thus be useful for research, therapeutics or diagnostics. Such uses include clinical uses in both medical and veterinary applications.

Thus, a somatostatin polypeptide of the invention, or a bioactive analog or subunit thereof, as well as those identified via the method of the invention, can be administered to an organism to function therapeutically as a somatostatin agonist or antagonist. The potential pharmacological uses of such somatostatins are numerous. For example, hypersecretion from endocrine tumors in the pituitary (e.g., acromegaly, TSH-secreting) or gastroenteropancreatic tissues (e.g., gastrinoma, VIPoma, glucagonoma, carcinoid syndrome) can be treated with somatostatin. In addition to the inhibition of hormone secretion, somatostatin analogs also may cause tumor shrinkage via their effects on cell proliferation and apoptosis. Another potential use of novel somatostatins or analogs is a adjuncts in the treatment of diabetes mellitus (via inhibition of growth hormone and glucagon). In addition, dysfunctional somatostatin secretion has been associated with AIDS and various neurological disorders (e.g., epilepsy, Alzheimer and Huntington diseases) and a somatotstatin antagonist might be effective in the treatment of such conditions. Nucleic acids encoding the somatostatin polypeptides of the invention, including bioactive analogs and subunits thereof, are potentially useful in gene therapy.

The invention also envisions fusing a plurality of N-terminal amino acids of a PPSS-I or PPSS-II" isoform or isoform fragment to peptides other than somatostatin so as to target them to somatostatin receptor molecules. The C-terminal peptide of the resulting fusion polypeptide preferably contains a bioactive peptide or other moiety. Different cell types in an organism are known to express different somatostatin receptors, making tissue specific targeting of bioactive moieties possible. For example, the fusion peptide could be targeted to neoplasms and their metastases, inhibiting the release of their secretory products and, possibly, providing access to the interior of the cell via internalization of the somatostatin receptor-ligand complex. The plurality of N-terminal amino acids of a PPSS-I or PPSS-II" isoform or isoform fragment preferably includes at least 7 contiguous amino acids, more preferably at least 10 contiguous amino acids, and most preferably at least 12 contiguous amino acids. The fusion protein is preferably made using recombinant DNA technology, but can be synthesized enzymatically or chemically as well. The invention thus includes a method for making the fusion peptide, as well as the resulting fusion peptide.

EXAMPLES

The present invention is illustrated by the following examples. It is to be understood that the particular examples, materials, amounts, and procedures are to be interpreted broadly in accordance with the scope and spirit of the invention as set forth herein.

Example I

Isolation, Cloning and Sequencing of PPSS-I from Rainbow Trout

Experimental Animals

Juvenile rainbow trout (*Oncorhynchus mykiss*), approximately 12 months of age, were obtained from the Garrison National Hatchery near Riverdale, N. Dak. The fish were maintained in dechlorinated, well-aerated municipal water at a temperature of 14° C. and were placed on a 12L:12D photoperiod. The fish were fed Glenco Mills (Glenco, Minn.) trout chow ad libitum twice daily and fasted for 24 hours before experimentation. The animals were anesthetized with 0.01% (w/v) tricaine methanesulfonate (MS-222) and sacrificed by a sharp blow to the head. Principal islets (Brockmann Bodies) as well as other tissues (brain, stomach, intestine, pyloric cecum, esophagus, kidney and liver) were removed from animals of both sexes. Tissues (ca. 50–100 mg) were placed in 2-ml microfuge tubes, frozen immediately on dry ice, then stored at –90° C. until subjected to RNA extraction (usually within two weeks).

RNA Extraction

Total RNA was prepared by a modification of the RNAzol method (Chomczynski et al., *Anal. Biochem.*, 162(1): 156–159 (1987)). Five hundred microliters of RNAzol (Cinna/Biotecx Laboratories, Friendswood, Tex.) was added to 2-ml microfuge tubes containing frozen tissue (approximately 25 mg), and the tissue was homogenized. Fifty microliters of chloroform were added to the tubes, and the mixture was vortexed for 30 seconds and incubated at 4° C. for 15 minutes. Following centrifugation at 1200 g for 15 minutes at 4° C., the aqueous phase was carefully removed and transferred to a sterile 1.5 ml microfuge tube. An equal volume of isopropanol was added, and the RNA was precipitated for 2 hours at –20° C. RNA was recovered as a pellet by centrifugation at 1200 g at 4° C. for 20 minutes and resuspended in 100 µl of sterile water. A second precipitation was performed by adding 50 µl of 5 M NaCl and 250 µl of absolute ethanol, followed by an incubation of the mixture at –20° C. overnight. Following the second precipitation, RNA was again recovered by centrifugation for 20 minutes at 1200 g at 4° C. The RNA pellet was vacuum dried for 2–5 minutes to remove any residual ethanol and resuspended in 75 µl of sterile water. Total RNA was quantified by UV $A_{260}$ spectrophotometry and diluted to 15 µg/µl. RNA samples were stored at –90° C. until used.

Oligonucleotide Primers and cDNA Probes

National Biosciences (Plymouth, Minn.) custom synthesized the gene-specific oligonucleotides used in reverse transcription and polymerase chain reaction (PCR). The GSP-1 primer was designed from degenerate conserved regions of the cDNAs encoding human (Shen et al., *Proc. Natl. Acad. Sci. USA*, 79, 4575–4579 (1982), rat (Goodman et al., *J. Biol. Chem.*, 258, 570–573 (1983), anglerfish I (Goodman et al., *Proc. Natl. Acad. Sci. USA*, 77, 5869–5873 (1980); Hobart et al., *Nature*, 288, 137–141, (1980), and catfish I (Minth et al., *J. Biol. Chem.*, 257, 10372–10377 (1982) somatostatins. Additional primers used for PCR were obtained from Gibco/BRL (Gaithersburg, Md.).

The full-length SS-I cDNA probe was made by reverse transcription PCR using primers designed from the SS-I cDNA sequence and purified by ultrafiltration using a 100,000 M.W. cutoff filter (Millipore, Bedford, Mass.) followed by ethanol precipitation (¼ volume 5M NaCl, 2 volumes absolute ethanol) at –20° C. overnight. After the cDNA probe was recovered by centrifugation (12,000×g, for 20 minutes at 4° C.), it was resuspended in 100 µl sterile water and quantitated by UV $A_{260}$ spectrophotometry. The full-length SS-I cDNA probe was radiolabeled with [$\alpha^{32}$P]-CTP by nick translation (Nick Translation System; Promega) according to the manufacturer's protocol. The probe was purified over Elutip-D columns (Schleicher and Schuell) according to the manufacturer's protocol.

Isolation and Sequence Analysis of Preprosomatostatin cDNAs

A two-phase rapid amplification of cDNA ends (RACE) PCR-based approach (FIG. 4) was used for the isolation and characterization of selected cDNA sequences as described previously (Moore et al., *Gen. Comp. Endocrinol.*, 253–261 (1995). In phase I, endogenous poly-A RNA was reverse transcribed from 15 µg of trout pancreatic total RNA with Superscript II reverse transcrptase (Gibco/BRL, Gaithersburg, Md.) and a 37 nucleotide antisense adapter primer 5'-GGCCACGCGTCGACTAGTAC(T)$_{17}$-3' (SEQ ID NO:22) (Gibco/BRL). Five microliters of the reverse transcription reaction were used as template for 3'-RACE PCR with a 21-base somatostatin gene-specific primer 5'-AAGAACTTTGGAAGACC-3' (GSP-1; SEQ ID NO:25) and the universal amplification primer 5'-CUACUACUA CUAGGCCACGCGTCGACTAGTAC-3'(UAP; SEQ ID NO:23). After an initial denaturation cycle of 94° C. for 5 minutes, 35 PCR cycles were performed, each consisting of 1-minute annealing (42° C.), 1-minute extension (72° C.), and 1 -minute denaturation (94° C. ). In the last cycle, the extension time was increased to 10 minutes to ensure complete extension. The resulting PCR product, (350 bp) was identified by electrophoresis on an agarose gel containing 1% (w/v) agarose (Gibco/BRL) and 1% (w/v) NuSeive GTG agarose (FMC Bioproducts, Rockland, Me.) in 1×TBE Buffer, followed by ethidium bromide staining and UV transillumination. Amplified fragments were directly cloned into the TA cloning vector PCR 2000. (Invitrogen, San Diego, Calif.). Positive colonies were identified by agarose gel electrophoresis of restriction enzyme digests (EcoRI; Promega, Madison, Wis.) of purified plasmid preparations (Del Sal et al., *BioTech.*, 7, 514–519 (1989)). One to 2 µg of plasmid were denatured and sequenced by the dideoxy chain-termination method (Sequenase Kit; U.S. Biochemicals Corp., Cleveland, Ohio) according to the manufacturer's protocol. All sequences were confirmed by sequencing multiple colonies from at least three independent PCR reactions and with two or more different primers in both directions, with dGTP didoexy nucleotides. Sequencing gels were made with 30% formamide to eliminate the possibility of G/C compressions.

In phase II (FIG. 4), isolation of the 5' cDNA sequence was accomplished by 5'-RACE PCR (Gibco/BRL). Somatostatin mRNA was exclusively reverse transcribed from pancreatic total RNA using a 20-base antisense oligonucleotide primer complementary to a region of the 3' fragment isolated in phase I 5'-ATTCATTAACACGATGTAAA-3' (GSP-2; SEQ ID NO:26). The resulting cDNA was purified twice over Glass Max spin columns (Gibco/BRL) to remove unincorporated dNTPs and primer and "tailed" at the 3' end with dCTP using terminal deoxynucleotidyl transferase (Gibco/BRL). Five microliters of the tailing reaction were used as template for 5'-RACE PCR with GSP-2 (SEQ ID NO:26) and anchor primer 5'-CUACUACUACUAGG CCACGCGTCGACTAGTACGGGIIGGGIIGGGIIG-3' (SEQ ID NO:24) (Gibco/BRL). Thirty-five PCR cycles were performed as in 3'-RACE PCR, except Taq polymerase (Perkin-Elmer, Norwalk, Conn.) was pipetted beneath the layer of mineral oil after the initial 5-minute denaturation cycle (Mullis, *PCR Meth. Appl.*, 1, 1–4 (1991). The amplified product (452 bp) was identified by agarose gel electrophoresis, cloned, and sequenced.

Data Analysis

Nucleotide and deduced amino acid sequences were aligned and analyzed with the OMIGA 1.0 DNA/protein analysis program (Oxford Molecular Group, Campbell, Calif.).

Characterization of cDNA Clones

Sequence analysis of the 350-bp 3' RACE PCR product revealed a region of 33 nucleotides that is 87.8% identical to the last 33 nucleotides of the human somatostatin coding region (Shen et al., *Proc. Natl. Acad. Sci. USA* 79, 4575–4579 (1982); the rest of the 350-bp fragment consisted of the 3'-untranslated region, including a polyadenylated tail at the most 3' end. The presence of a portion of the somatostatin coding region in the amplified product suggested the successful isolation of a pancreatic preprosomatostatin gene 1 fragment. Sequence analysis of the 452-bp 5' RACE PCR product revealed the complete somatostatin coding region and the full 5'-untranslated region. Overlapping sequence of the two fragments identified a 745-bp cDNA containing the complete 5'-untranslated region, a single initiation site 118 bases from the most 5' end, and a single putative polyadenylation site 17 bases from the most 3' end that was terminated with a polyadenylated tail. The existence of only one PPSS-I mRNA was indicated after exhaustive screening; some 15–10 colonies from each of three independent PCR reactions were sequenced.

Analysis of Deduced Protein

FIG. 2 shows a nucleotide sequence contained an open reading frame of 342 bases that encodes for a preprosomatostatin molecule 114 amino acids in length (SEQ ID NO:3). The predicted preprosomatostatin molecule possesses a putative signal sequence of 24 amino acids (SEQ ID NO:7, overlined in FIG. 2). The deduced protein contains a number of putative processing sites, potentially yielding a 26-amino acid peptide (SEQ ID NO:4) that could be processed further to a 14-amino acid peptide (SEQ ID NO:1) identical in structure to mammalian SS-14, confirming that the precursor is a PPSS-I.

A comparison of rainbow trout PPSS-I cDNA with other cDNA nucleotide sequences (FIG. 5) reveals that rainbow trout PPSS-I (TRI) is most similar to catfish PPSS-I (CFI) with a percent identity of 77.0%. Notably, rainbow trout PPSS-I is more similar to the preprosomatostatin I cDNAs than to the rainbow trout PPSS-II' and PPSS-II" cDNAs.

The deduced PPSS-I protein (SEQ ID NO:3) produced in rainbow trout islet cells contains 114 amino acids, the same number of amino acids as catfish PPSS-I but slightly shorter than the 121-amino acids precursor of anglerfish I. The deduced amino acid sequence of rainbow trout PPSS-I exhibits 73.5% identity with catfish I and chicken. Rainbow trout PPSS-I was the least similar to anglerfish I, with an identity of 58.1%. Amino acid identities between rainbow trout PPSS-I and rainbow trout PPSS-II' and PPSS-II" were lower; identities were 49.0% and 48.2%, respectively. It would appear that evolutionary selection has acted to conserve the structure of the whole preprosomatostatin I molecule (Argos et al., *J. Biol. Chem.*, 258, 8788–8793 (1983)).

While the details concerning the processing of rainbow trout preprosomatostatin I are not known, a basic pattern emerges from the deduced amino acid sequence. Analysis of the first 25 amino acids of the molecule indicates that this segment fulfills all of the criteria for a signal sequence established by Pugsley, *Protein Targeting*, Academic Press, New York (1989). The putative signal sequence of rainbow trout preprosomatostatin I is similar to the known signal sequences reported for human and rat preprosomatostatin I (Conlon et al., *Biochem. J.*, 248 123–127 (1987); Goodman et al., *J. Biol. Chem.*, 258, 570–573 (1983)) and to other leading sequences reported for preprosomatostatin I. Based on the presence of Arg monobasic and Arg-Lys dibasic cleavage sites (FIG. 2), we propose that rainbow trout prosomatostatin I gives rise to peptides 26 amino acids (SEQ ID NO:4) and/or 14 amino acids (SEQ ID NO:1) in length.

FIG. 6 shows a comparison of rainbow trout SS-I with other somatostatin gene 1 peptide sequences either isolated from islet tissue or deduced from cDNAs. There has been strong conservation of the C-terminal regions (up to 19 residues); only the sequence of hagfish differs with two amino acid substitutions of glycine for proline and proline for alanine at positions 18 and 20. Perhaps most interesting is the difference in the number of amino acids. All PPSS-Is examined possess cleavage sites potentially yielding a 28-amino acid peptide with SS-14 at its C-terminus. Rainbow trout PPSS-I is unique because it potentially gives rise to a 26-amino acid peptide containing SS-14 at its C-terminus. This difference was due to a 6-nucleotide deletion in the somatostatin coding region. Bowfin, a non-teleost ray-finned fish, has been reported to possess a modified SS form with 26 amino acids that contains [Ser$^5$]-SS-14 at its C-terminus (Wang et al., *Regul. Peptides*, 47, 33–40 (1993)).

Example II

Differential Expression of PPSS-I Expression in Tissues of Rainbow Trout

The distribution of PPSS-I mRNA in various tissues was investigated by northern blot analysis. Total RNA from rainbow trout brain, pancreas, stomach, intestine, esophagus, pyloric ceacum, kidney, and liver was isolated by the RNAzol method (Chomczynski et al., *Anal. Biochem.*, 162(1):156–159 (1987)). Ten micrograms of total RNA from each tissue were separated on a formaldehyde-agarose denaturating gel and transferred onto a 0.45-$\mu$m nylon support (Micron Separations Inc.) by diffusion overnight. The membrane was baked under a vacuum at 85° C. for 2 hours and prehybridized in hybridization solution (5×SSPE, 5×Denhardt's solution, 0.1% SDS) containing 0.1 mg/ml denatured calf thymus for 2 hours at 37° C. The prehybridization mixture was removed, and the membrane was hybridized at 37° C. overnight in hybridization solution containing a full-length SSI cDNA radiolabeled (1×10$^6$ CPM/ml) probe. The blot was washed twice with 2×SSPE containing 0.2% (v/v) SDS for 20 minutes at 65° C. and once with 0.1×SSPE at 65° C. for 20 minutes. Autoradiography was performed by exposing the blot to Fuji RX film for 48 hours at −90° C.

Hybridization with a SS-I full-length cDNA probe revealed a single transcript approximately 750-bp in length in the pancreas, brain, stomach, and intestine. There was no apparent signal in the other tissues examined. Thus, Northern analysis revealed that PPSS-I was expressed in the pancreas, stomach, intestine, and brain of rainbow trout. This result is the first report of PPSS-I in extrapancreatic tissues of fish. The presence of the precursor molecule in the various tissues noted, however, is consistent with the brain-gut distribution of SS observed in mammals (Gerich, in: *Diabetes Mellitus: Theory and Practice*, Medical Examinations Publishing, New York, 225–254 (1983)). The presence of a single band suggests that the expression of SS gene 1 in rainbow trout results in the production of a single mRNA species. The existence of a single transcript also suggests the expression of single SS gene 1. This result is noteworthy since it has been inferred from cDNA evidence that rainbow trout has two SS genes giving rise to PPSS-II, SS-I', and SS-II", presumably because of the tetraploid (Ohno, *Evolution by Gene Duplication*, Springer-Verlag, Berlin, 1970) nature of the species. The lack of a second somatostatin gene 1 in extant trout could be explained by an incomplete duplication associated with the autotetraploidation event that gave rise to the two somatostatin gene 2s or by the secondary loss of the alternate somatostatin gene 1.

This present study contributes to the growing body of evidence that suggests the existence of multiple somatostatin genes in vertebrates. Based on cDNA and peptide sequence information, multiple somatostatin genes appear to exist in lamprey, teleost fish, and frogs (Conlon et al., *Regul. Peptides* 69, 95–103 (1997)). Whether these genes arose form a single duplication event prior to the emergence of lamprey or from separate duplication events is uncertain (Conlon et al., *Regul. Peptides*, 69, 95–103 (1997); Sheridan et al., *Advances in Comparative Endocrinology*, 1, 291–294 (1997)). Regardless, the widespread distribution of PPSS I and PPSS II in teleosts indicate the emergence of separate genes for these precursors prior to the divergence of this group. Future research on other taxa will provide additional insight into the evolution of the somatostatin gene family.

Example III

Isolations Cloning and Sequencing of PPSS-II" From Rainbow Trout

Experimental Animals

Juvenile rainbow trout, *Oncorhynchus mykiss*, were obtained from the Garrison National Fish Hatchery near Riverdale, N. Dak. Fish were maintained at North Dakota State University in well-aerated, dechlorinated municipal fresh water (14° C.) under 12L:12D photoperiod and fed to satiety twice daily with Supersweet Feeds (Glenco, Minn.) trout grower except 24 hours prior to experiments. In the nutritional state experiment, fish were either fed as usual or fasted for two weeks prior to sample collection.

RNA Extraction

Tissues were removed from rainbow trout of both sexes after the animals had been anesthetized with 0.01% (w/v) 3-aminobenzoic acid ethyl ester (MS-222, Sigma) buffered with 0.2% (w/v) sodium bicarbonate. Tissue samples (approximately 25 mg) were placed in 2-ml microfuge tubes and immediately frozen on dry ice. Total RNA was extracted by a modification of the RNAzol method (Cinna/Biotecx Laboratories, Friendswood, Tex.) described previously in Moore et al., *Gen. Comp. Endocrinol.*, 98, 253–261 (1995). Total RNA was quantified by UV A$_{260}$ spectrophotometry and diluted to 15 $\mu$g/$\mu$l. RNA samples were stored at −90° C. until used.

Primers and Probes

Oligonucleotides were either custom synthesized by National Biosciences (Plymouth, Minn.) or supplied with Gibco/BRL 3'- and 5'-RACE kits. Oligonucleotides used as probes were 5'-end labeled with [$\gamma^{32}$P]-ATP (Amersham) using T4-polynucleotide kinase (Promega) as previously described in Sambrook et al., *Molecular Cloning: A Laboratory Manual*, 2$^{nd}$ Edition, Plainview, N.Y., Cold Spring Harbor Laboratory Press (1989). The full-length SS-II cDNA probe was radiolabeled with [$\alpha^{32}$P]-CTP by random priming (Prime-a-Gene; Promega) according to the manufacturer's protocol. All radiolabeled probes were purified over Elutip-D columns (Schleicher and Schuell) according to the manufacturer's protocol.

Isolation and Sequence Analysis of Preprosomatostatin cDNA

A two-phase rapid amplification of cDNA ends (RACE) PCR-based approach (FIG. 4) was used for the isolation and characterization of selected cDNA sequences as described previously in Moore et al., *Gen. Comp. Endocrinol.*, 98, 253–261 (1995). Briefly, in phase I, endogenous poly-A RNA was reverse transcribed from 15 $\mu$g of trout pancreatic total RNA with Superscript II reverse transcriptase (Gibco/BRL, Gaithersburg, Md.) and a 37-nucleotide antisense adapter primer (Gibco/BRL). Five microliters of the reverse transcription reaction were used as template for 3-RACE PCR with a 21-base somatostatin gene-specific primer (GSP-1; 5' GGCTGCAAGAATTTCTTCTCG 3') (SEQ ID NO:33) and the universal amplification primer (UAP; SEQ ID NO:23; Gibco/BRL). After an initial denaturation cycle of 94° C. for 5 minutes, 39 PCR cycles were performed, each consisting of 1 minute denaturation (94° C.), 1 minute annealing (42° C.), and 1 minute extension (72° C.). In the last cycle, the extension time was increased to 10 minutes to ensure complete extension. The resulting PCR product was identified by electrophoresis on an agarose gel containing 1% (w/v) agarose (Gibco/BRL) and 2% (w/v) NuSeive GTG agarose (FMC Bioproducts, Rockland, Me.) in 1×TBE followed by ethidium bromide staining and UV transillumination. Amplified fragments were directly cloned into the TA cloning vector PCR 2000 (Invitrogen, San Diego, Calif.). Positive colonies were identified by agarose gel electrophoresis, as described above, of restriction enzyme digests (EcoRI; Promega, Madison, Wis.) of purified plasmid preparations as previously described in Del Sal et al., *Biotechniques*, 7, 514–519 (1989). One to 2 μg of plasmid DNA was denatured and sequenced by the dideoxy chain-termination method (Sequenase Kit; U.S. Biochemicals Corp., Cleveland, Ohio) according to the manufacturer's protocol. All sequences were confirmed by sequencing multiple colonies from at least three independent PCR reactions and with two or more different primers in both directions.

In phase II (FIG. 4) isolation of the 5' cDNA sequence was accomplished by 5'-RACE PCR (Gibco/BRL). Somatostatin mRNA was exclusively reverse transcribed from pancreatic total RNA using a 20-base antisense oligonucleotide primer complementary to a region of the 3' fragment isolated in phase I (GSP-2; 5' GTTGGCGGTGTGACGTGATTG 3') (SEQ ID NO:34). The resulting cDNA was purified twice over Glass Max spin columns (Gibco/BRL) to remove unincorporated dNTPs and primer and then "tailed" at the 3' end with dCTP using terminal deoxynucleotidyl transferase (Gibco/BRL). Five microliters of the tailing reaction were used as template for 5'-RACE PCR with GSP-2 (SEQ ID NO:34) and anchor primer (SEQ ID NO:24; Gibco/BRL). Thirty-nine PCR cycles were performed as in 3'-RACE PCR, except Taq polymerase (Perkin-Elmer, Norwalk, Conn.) was pipetted beneath the layer of mineral oil after the initial 5-min denaturation cycle as previously described in Mullis, *PCR Methods Appl.*, 1, 1–4 (1991). The 243 bp amplified product was identified by agarose gel electrophoresis, cloned, and sequenced as described above.

Data Analysis

Nucleotide and deduced amino acid sequences (coding regions only) were aligned and analyzed with the DOS-based PsiNine DNA/protein analysis program (North Dakota State University, Department of Biochemistry) and OMIGA 1.0 for Windows 95/NT (Oxford Molecular Group, Campbell, Calif.). Quantitative data are expressed as means±S.E.M. The two-tailed Student t-test was used to estimate differences between treatment groups. A probability level of 0.05 was used to indicate significance. All statistics were performed using SigmaStat (Jandel Scientific, Palo Alto, Calif.).

Rainbow Trout Possess Two cDNAs Encoding Preprosomatostatins That Contain [Tyr$^7$, Gly$^{10}$]-somatostatin-14

Sequence analysis of the 243 bp 3' fragment revealed six codons followed by a stop codon with 100% identity to the last six codons (+9 to +14) of trout PPSS-II containing [Tyr$^7$, Gly$^{10}$]-SS-14 recently identified and reported by our laboratory (Moore et al., *Gen. Comp. Endocrinol.*, 98, 253–261 (1995); the remainder of the fragment consisted of 3'-untranslated region, including a polyadenylated tail at the most 3' end. Reverse transcription and 5'-RACE PCR with the GSP-2 primer resulted in the amplification of a 561-bp fragment identical in sequence to that which we reported previously in Moore et al., *Gen. Comp. Endocrinol.*, 98, 253–261 (1995). Reverse transcription and 5'-RACE PCR with a newly-designed antisense primer unique to the new 3' fragment resulted in the amplification of a 544-bp fragment. Overlapping sequence of the 243-bp 3'-RACE and 544-bp 5'-RACE fragments identified a novel 600-bp cDNA (SEQ ID NO:20) encoding for a second preprosomatostatin containing [Tyr$^7$, Gly$^{10}$]-SS-14, which we have designated PPSS-II" (SEQ ID NO:15), with a single putative initiation site 101 bases downstream from the most 5' end and two putative polyadenylation signal sites. Exhaustive screening of 18–23 colonies from each of three independent 3' RACE and 5' RACE PCRs confirmed the existence of only two cDNAs, one encoding PPSS-II" (SEQ ID NO:20) and one identical to our previously reported sequence (SEQ ID NO:14) (Moore et al., *Gen. Comp. Endocrinol.*, 98, 253–261 (1995)) which encodes for the precursor we now designate PPSS-II'.

A comparison between PPSS-II" cDNA (SEQ ID NO:20) and our previously reported PPSS-I' cDNA sequence (Moore et al., *Gen. Comp. Endocrinol.*, 98, 253–261 (1995) (SEQ ID NO:14) is shown in FIG. 3. While PPSS-II' is a 115-amino acid protein (SEQ ID NO:9) containing numerous putative recognition sites for post-translational modification by converting enzymes, potentially yielding a 28-amino acid somatostatin peptide (SEQ ID NO:10) with [Tyr$^7$, Gly$^{10}$]-SS-14 at its C-terminus, PPSS-II" is a 111-amino acid protein (SEQ ID NO:15) potentially processed to a 25-amino acid somatostatin peptide (SEQ ID NO:16) containing [Tyr$^7$, Gly$^{10}$]-SS-14 at its C-terminus. Somatostatin-II' and SS-II" share 82.3% nucleotide and 80.5% amino acid identity.

Despite the similarity of sequence between SS-II' and SS-II", we took advantage of a 50 base region immediately upstream from the C-termini of the SS coding regions to design three 20-base oligonucleotides that would specifically bind to SS-II' mRNA, SS-II" mRNA, or to both SS-II' and SS-II" mRNAs (the specificity of these probes was verified by hybridization to in vitro synthesized RNA). Northern analysis using these probes revealed that there was a single transcript encoding PPSS-II' and a single transcript encoding PPSS-II".

The present study characterized two cDNAs that encode preprosomatostatins containing [Tyr$^7$, Gly$^{10}$]-SS-14 at their C-terminus (designated PPSS-II', SEQ ID NO:14, and PPSS-II", SEQ ID NO:20) and demonstrated that the two PPSS-II mRNAs are differentially expressed. This is the first report of the coexistence of two different PPSS-IIs. The nucleotide identity between the two cDNAs is 82.3%; the position and extent of the differences suggests the existence of two nonallelic PPSS-II genes. The two PPSS-IIs in rainbow trout (SEQ ID NOs:9 and 15) are in addition to a single PPSS-I (SEQ ID NO:3) containing SS-14 at its N-terminus, which also presumably arise from a separate gene as described in Kittilson et al., *Gen. Comp. Endocrinol.* 114, 88–96(1999).

The deduced PPSS-II' (SEQ ID NO:9) and PPSS-II" (SEQ ID NO: 15) proteins in rainbow trout Brockmann bodies contain 115 and 111 amino acids, respectively, both slightly shorter than the precursors of anglerfish (Goodman et al., *J. Biol. Chem.*, 258, 570–573 (1983);Goodman et al., *Proc. Natl. Acad. Sci. USA* 77, 5869–5873 (1980); and Hobart et al., *Nature*, 288, 137–141 (1980)), and goldfish (Lin et al., *Endocrinology*, 140, 2089–2099 (1999)), the only other known PPSS-IIs containing [Tyr$^7$, Gly$^{10}$]-SS-14. Rainbow trout PPSS-II' shared 43.5% amino acid identity with anglerfish PPSS-II and 51.3% amino acid identity with goldfish PPSS-II. The amino acid identity between rainbow trout PPSS-II" and anglerfish PPSS-II was 38.7% while the identity between trout PPSS-II" and goldfish PPSS-II was 41.4%. Amino acid identities between rainbow trout PPSS-IIs and precursors derived from gene 1 were lower, between 37.9% and 22.5%. Rainbow trout PPS-IIs were least similiar the preprosomatostatin giving rise to catfish SS-22. Although the evidence is limited, it appears that evolutionary selection has acted to conserve the biologically active C-terminal domain of PPSSs (see FIG. 7).

A comparison of nucleotide and predicted amino acid sequences between SS-II' and SS-II" of rainbow trout also helps to resolve questions surrounding the heterogeneity of the SS gene 2 family of peptides among teleosts. For example, 25-amino acid peptides with [$Tyr^7$, $Gly^{10}$]-SS-14 at their C-terminus were isolated from eel, Conlon et al., *Gen. Comp. Endocrinol.*, 72, 181–189 (1988), and coho salmon, Plisetskaya et al., *Gen. Comp. Endocrinol.*, 63, 252–263 (1986), whereas 28-amino acid peptides with [$Tyr^7$, $Gly^{10}$]-SS-14 have been isolated from anglerfish, Hobart et al., *Nature*, 288, 137–141 (1980), flounder, Conlon et al., *Gen. Comp. Endocrinol.*, 72, 181–189 (1988), goldfish, Uesaka et al., *Gen. Comp. Endocrinol.*, 99, 298–306 (1995), sculpin, Conlon et al., *Gen. Comp. Endocrinol.*, 72, 181–189 (1988), and tilapia, Nguyen et al., *Comp. Biochem. Physiol. C. Pharmacol. Toxicol. Endocrinol.*, 111C, 33–44 (1995). The present findings in trout, in which PPSS-II' possesses a putative Arg processing site that would give rise to a 28-amino acid peptide containing [$Tyr^7$, $Gly^{10}$]-SS-14 and in which PPSS-II" possesses a putative Arg processing site that would give rise to a 25-amino acid peptide containing [$Tyr^7$, $Gly^{10}$]-SS-14, suggest that the difference between the 28- and 25-amino acid forms results from a nine nucleotide deletion in the SS coding region.

Example IV

Differential Distribution of PPSS-II" in Tissues of Rainbow Trout

RNA template-specific PCR

The expression of PPSS-II' and PPSS-II" mRNAs was qualitatively evaluated in various tissues using RNA template-specific PCR (RS-PCR) because of its high specificity (amplification of false positives derived from contaminating genomic DNA is excluded) and high sensitivity as previously described in Shuldiner et al., *Biotechniques*, 11, 760–763 (1991). A $d_{17}t_{30}$ primer (5' CATGTACCTTGAT-CAACCGTCACGTGGCAGCCAGTAGAA GTTCTTGC 3') (SEQ ID NO:50), containing 17 bases at its 3' end complementary to both SS-II' and SS-II" ($d_{17}$), and 30 bases of non-specific tagging sequence at its 5' end ($t_{30}$), was used to co-reverse transcribe PPSS-II' and PPSS-II" mRNA in total RNA isolated from tissues. Five microliter (15 μg) duplicate aliquots of total RNA were placed in 0.5-ml microfuge tubes and either stored at 4° C. or incubated with 5 units of RNase-A (Sigma) for 30 minutes at 37° C. Following RNase-A pretreatment, the remaining reaction components were added to both tube sets (20 μl total volume) so that the final composition was 20 mM Tris-HCl (pH 8.4), 50 mM KCl, 2.5 mM $MgCl_2$, 100 μg/ml BSA, 10 mM DTT, 0.5 μM primer, 2 mM dNTP's, and 5 units of AMV reverse transcriptase (Promega). The reactions were incubated at 37° C. for 1 hour and stored on ice until used as template for PCR. Five microliters of the reverse transcription reaction were used as template for PCR in a final reaction containing 50 mM KCl, 10 mM Tris-HCl (pH 8.3 at 25° C.), 1.5 mM $MgCl_2$, 0.01 mg/ml gelatin, 200 μM of each dNTP, 0.5 μM upstream somatostatin $u_{30}$ primer (5' ATTTGCAGCCAAGGAGCCGCCTCGCAGCC 3') (SEQ ID NO:51), 0.5 μM downstream $t_{30}$ primer (identical to the $t_{30}$ region of the $d_{17}t_{30}$ primer; 5' CATGTACCTTGAT-CAACCGTCTCGTGGCAG 3') (SEQ ID NO:52), and 0.04 units of Taq DNA polymerase (Perkin Elmer) overlaid with 50 μl of sterile mineral oil. To increase specificity, the annealing temperature was raised to 65° C., and thirty-nine PCR cycles were performed as described previously.

The resulting RS-PCR products were subjected to Southern blot analysis. The amplified cDNAs were separated by agarose gel electrophoresis as described above and the gel was blotted by capillary transfer to 0.45 μm nitrocellulose membrane (Schleicher and Schuell) overnight as previously described in Sambrook et al., *Molecular Cloning: A Laboratory Manual*, $2^{nd}$ Edition, Plainview, N.Y., Cold Spring Harbor Laboratory Press (1989). The membrane was baked in a vacuum oven (80° C.) for 2 hours and pre-hybridized in hybridization solution [5×SSPE (20×solution: 3 M NaCl, 0.2 M $NaH_2PO_4$, 0.02 M EDTA-$Na_2$), 5×Denhardt's solution (100×solution: 10 g polyvinylpyrrolidone, 10 g BSA, 10 g Ficoll 400, $H_2O$ to 500 ml), 0.5% (v/v) sodium dodecyl sulfate] containing 0.1 mg/ml denatured salmon sperm DNA for 2 hours at 37° C. The prehybridization mixture was removed and the membrane was hybridized at 37° C. overnight in hybridization solution containing 353-base SS-II cDNA radiolabeled ($1 \times 10^6$ CPM/ml) probe. The blot was washed twice with 2×SSPE containing 0.2% (v/v) SDS for 20 minutes at 65° C. and autoradiography was performed (30 hours exposure at −90° C. using Fuji RX film).

Slot-blot Quantitation of mRNA

To determine which of the two mRNA species (PPSS-II' and PPSS-II") were expressed within various tissues, RS-PCR products were subjected to slot-blot analysis as previously described in Celi et al., *Gen. Comp. Endocrinol.*, 95, 169–177 (1994), a technique similar to RNase protection assay in that it relies upon reference to in vitro-synthesized RNA standards and has a sensitivity of ca. $10^6$ molecules, but lends itself more readily to the analysis of numerous samples. cRNA standards were made by first cloning full-length SS-II' and SS-II" cDNAs in the sense orientation into the PCR 2000 cloning vector (Invitrogen). After linearization with ecoRV (Promega; for SS-I' inserts) or BamHI (Promega; for SS-II" inserts), in vitro RNA synthesis was performed using T7 RNA polymerase (40 units; Promega), according to the manufacturer's protocol. Full-length cRNA was separated from unincorporated NTP's by ultrafiltration (100,000 M.W. cutoff; Millipore, Bedford, Mass.) followed by ethanol precipitation (¼ volume NaCl, 2×volume absolute ethanol) at −20° C. overnight. After recovery of RNA by centrifugation (12,000×g, for 20 minutes at 4° C.), RNA was resuspended in 100 ml sterile water and quantitated by UV $A_{260}$ spectrophotometry. The homogeneity of cRNA standard preparations was assessed by electrophoresis on a 6% polyacrylamidel 8.0 M urea gel and verified by sequence analysis. Northern analysis was performed as previously described in Kittilson et al., *Gen. Comp. Endocrinol.*, 114, 88–96 (1999) to evaluate the number and size of transcripts as well as to verify that the specific oligonucleotide probes hybridized only with SS-II" and SS-II" transcripts in the total RNA extracted from the Brockmann bodies of trout. Four hundred-fifty microliter replicate dilutions of standards [serially diluted in sterile water containing yeast tRNA (10 μg/ml) and RNasin (80 units/ml; Promega)] and pancreatic total RNA samples [10 μg were initially diluted with sterile water to a final volume of 50 μl to which was added 20 μl of 37% formaldehyde and 30 μl of 20×SSC (3 M NaCl, 0.3 M $Na_3C_6H_5O_7 \cdot 2H_2O$, pH 7.0). After incubation at 65° C. for 15 minutes, the RNA samples were immediately placed on ice and diluted further with 1000 μl of ice-cold 10×SSC.] were slotted directly onto 0.2 μm Nytran membrane (Schleicher and Schuell) and hybridized, individually, with either SS-II'-specific, SS-II"-specific or SS-II'/SS-II"-common (standards only; for normalization of RNA amount) radiolabeled oligonucleotide probes as described above. The resulting autoradiograms were quantified by scanning laser densitometry (Molecular Dynamics, Sunnyvale, Calif.). Statistical differences were estimated by a two-tailed Student t-test (n=12; $p<0.05$). Briefly, 10 μl of RS-PCR product were boiled for 5 min in a 1.5-ml microfuge tube and then immediately placed on ice and diluted with 1000 μl ice cold 5×SSPE. Four hundred-fifty microliters were then slotted in duplicate directly to 0.2 μm Nytran membrane (Schleicher and Schuell) using a Minifold II slot-blot apparatus (Schleicher and Schuell) under weak vacuum. The wells were washed twice with 500 μl of 5×SSPE and the membrane was allowed to air dry. The duplicate blots were baked, prehybridized, and hybridized with either SS-II'-specific or SS-II"-specific radiolabeled ($1 \times 10^6$ CPM/ml) oligonucleotide probes. The blots were then washed and autoradiographed as described above.

Two PPSS-II mRNAs are Differentially Expressed in Various Tissues

RNA from various tissues was extracted and reverse transcribed. The resulting cDNAs encoding for PPSS-II' and PPSS-II" were co-amplified by RS-PCR, electrophoresed on agarose, and subjected to Southern blot analysis using a full-length SS-II cDNA probe (which does not distinguish between SS-II' and SS-II"). With this approach, PPSS-II mRNA was detected in brain, esophagus, pyloric caeca, stomach, upper and lower intestine, and Brockmann bodies. Duplicate samples pre-treated with RNase demonstrated that amplified products were exclusively derived from RNA templates and not false positives derived from contaminating genomic DNA.

When slot-blot analysis of RS-PCR products was performed using gene-specific oligonucleotide probes that distinguish PPSS-II' and PPSS-II" mRNA, we detected the presence of PPSS-II' and PPSS-II" mRNA in esophagus, pyloric caeca, stomach, upper and lower intestine, and Brockmann bodies, while only PPSS-II" mRNA was present in brain.

Abundance of PPSS-II mRNAs is Different in Various Tissues

Hybridization of the gene-specific oligonucleotide probes to replicate slot-blots containing known quantities of in vitro-synthesized PPSS-II' and PPSS-II" cRNA standards, in the range of $6.5 \times 10^8$ to $5.0 \times 10^9$ molecules, and RNA extracted from selected tissues allowed for the accurate evaluation of the amounts of PPSS-I' and PPSS-II" mRNAs. We used this approach to examine the expression of PPSS-II' and of PPSS-II" mRNAs in Brockmann bodies (endocrine pancreas) and stomachs removed from animals under normal (fed to satiety twice per day except 24 hours before sampling) physiological conditions. Under these conditions, pancreatic SS-II" mRNA levels were nearly three-fold higher than those of SS-II', estimated to be $8.7 \times 10^8$ molecules/μg total RNA and $3.2 \times 10^8$ molecules/μg total RNA, respectively. The concentrations of PPSS-II mRNAs were lower in stomach than in pancreas. In addition, the relative abundance PPSS-II mRNA species in the stomach was opposite that in the pancreas such that the levels of PPSS-II' mRNA were ca. 10-fold higher than those of PPSS-II" mRNA.

Abundance of PPSS-II" mRNA is Modulated by Nutritional State

Nutritional state modulated the pattern of pancreatic PPSS-II mRNA expression. Fish that were fasted for two weeks displayed levels of PPSS-II" mRNA that were 2-fold higher than their continuously fed counterparts. The levels of PPSS-II' mRNA, however, were not affected by food deprivation.

The present study revealed that two PPSS-II mRNAs of rainbow trout are differentially expressed. This conclusion is based on several observations. First, the pattern of PPSS-II' mRNA and PPSS-II" mRNA is tissue-specific. For example, only PPSS-II" mRNA was detected in the brain of rainbow trout, whereas both PPSS-II' and PPSS-II" mRNA were detected in pancreas and various regions of the gut. Brain-specific expression of the mRNA encoding the alternate form of SS in frogs (denoted PSS2) (Tostivint et al., *Proc. Natl. Acad. Sci. USA.* 93. 12605–12610 (1996)) and cortistatin (de Lecea et al., *Nature* 381, 242–245 (1996)) also has been reported. Previous immunocytochemical studies support a similar distribution of [Tyr$^7$,Gly$^{10}$]-somatostatin-14-containing peptides in the intestine (Beorlegui et al., *Gen. Comp. Endocrinol.*, 86, 483–495 (1992)) and stomach (Barrenechea et al., *Tissue Cell,* 26 309–321 (1994)) of rainbow trout. Second, the abundance of PPSS-II mRNAs was different with specific tissues. Within the Brockmann body of rainbow trout, the predominant message form was that encoding for PPSS-II", whereas in the stomach the predominant form was that encoding PPSS-II'. Lastly, the pattern of PPSS-II expression within the endocrine pancreas of rainbow trout was modulated by nutritional state. Together, these results suggest that rainbow trout produce two forms of gene 2SS peptides and that there exists mechanisms to independently regulate the expression of each.

The alternate forms of somatostatin (containing [Tyr$^7$, Gly$^{10}$]-SS-14) in rainbow trout are in addition to SS-14 as previously described in Kittilson et al., *Gen. Comp. Endocrinol.,* 114, 88–96 (1999). The functions of the various somatostatin peptides remains to be fully elucidated; however, previous research has suggested that distinctive roles for the gene 1 and gene 2 forms exist. For example, peptides derived from gene 1 (e.g., SS-14, SS-28) were equipotent in their ability to inhibit the release of growth hormone from goldfish pituitary fragments in vitro, whereas peptides derived from alternate genes (e.g., salmonid SS-25, catfish SS-22) had no effect on growth hormone release as previously described in Marchant et al., *Fish Physiol. Biochem.* 7, 133–139 (1989). Similarly, salmonid SS-25 (from gene 2) inhibited insulin in rainbow trout, but SS-14 (from gene 1) did not as previously described in Eilertson et al., *Gen. Comp. Endocrinol.* 92, 62–70 (1993).

Example V

Competitive Binding of Somatostatins to Cloned Somatostatin Receptors

Somatostatin receptor cDNA was cloned into an expression vector, transfected into a eukaryotic cell line, and expressed as a peptide on the cell's surface to characterized the binding properties of the receptor for various somatostatin ligands.

Human Receptor Cloning

Human somatostatin receptor subtype I cDNA was graciously obtained from Dr. Graeme Bell at the University of Chicago. Clones were prepared substantially as described in Yamada et al., *Proc. Natl. Acad. Sci. USA,* 89, 251–255

(1992). Briefly, a cDNA library was created by inserting total cDNA into a cloning vector. Clones containing the cDNA inserts were digested with restriction endonuclease BglII and subsequently subcloned in the pCMV6b expression vector (Stratagene Zap Express cDNA Synthesis Kit, La Jolla, Calif.). The resulting expression vector containing the cloned somatostatin receptor was transfected into COS-7 (American Tissue Culture Collection, Manassas, Va.) cells for peptide expression.

Trout Receptor Cloning

Trout somatostatin receptor cDNA libraries can also be prepared substantially in accordance with the manufacturer's protocol (Stratagene Zap Express cDNA Synthesis Kit instruction manual; La Jolla, Calif.). Briefly, cDNA libraries are created by reverse transcribing mRNA (Stratagene kit) from rainbow trout brain. XhoI and EcoRI linkers are ligated to the ends of the cDNAs. The resulting cDNAs are then unidirectionally cloned into the pBK-CMV phagemid vector which is inserted into the ZAP Express lambda phage.

The phage are plated onto 150-mm petri dishes and lifted using a circular nitrocellulose membrane. The membranes are subsequently fixed by soaking them for approximately 2 minutes in 1.5M NaCl and 0.5M NaOH solution. Membranes are transferred to a 1.5M NaCl and 0.5M Tris-HCl solution at pH 8.0 for approximately 5 minutes. Finally, the membranes are soaked in a 0.2M Trish-HCl (pH 7.5) and 2×SSC solution for about 30 seconds.

The phage are screened by hybridization to rainbow trout somatostatin receptor probes. Trout somatostatin receptor sequence fragments are radiolabeled with $\alpha$-$^{32}$P dCTP (Amersham Pharmacia Biotech, Piscataway, N.J.) using a nick translation kit from Promega (Madison, Wis.). After hybridization, blots are exposed to Kodak X-ray film for 72 hours at −90° C. and developed.

Once positive colonies are found, the pBK-CMV phagemid contained within the phage is isolated by mass excision according to the Stratagene instruction manual. The resulting plasmid contains the cloned somatostatin receptor cDNA which can then be transfected into a eukaryotic cell line and the receptor peptide expressed on the cell surface.

Transfection of Eukaryotic Cell Lines

Twenty-four hours after splitting cells (e.g., COS-7) into new T-75 culture flasks (Nalgene, Rochester, N.Y.), the cells were washed with phosphate-buffered saline (PBS) and Tris-buffered saline-dextrose (TBS-D) solutions. A supercoiled or circular DNA/DEAE-dextran/TBS-D solution was prepared by mixing 0.1–4 $\mu$g/ml and 1.0 $\mu$g/ml DEAE-dextran in TBS-D. The DNA solution is removed and the cells are washed again with TBS-D and PBS solutions. Prewarmed medium (37° C.) supplemented with fetal bovine serum (Gibco BRL, Rockville, Md.) was added to the culture, along with chloroquine diphosphate (100 $\mu$M concentration) (Sigma, St. Louis, Mo.) and incubated for 3–5 hours in a humidified 37° C. incubator at 5% $CO_2$. The medium was removed and the cells are washed three times with serum-free medium. Medium supplemented with fetal bovine serum was added again and the cells were incubated for 30–60 hours in a humidified 37° C. incubator at 5% $CO_2$.

Membrane Preparation

The transfected eukaryotic cells were scraped from the culture flasks in a homogenizing buffer containing sucrose, Tris-HCl, phenylmethylsulfonyl fluoride, and aprotinin in distilled water. The cells remain on ice until homogenized. The cell suspension was homogenized in two, 15 second bursts. The homogenate was then centrifuged at 100,000×g for 20 minutes in a Beckman SW-28 rotor at 4° C. The supernatant was discarded and the pellet resuspended in a buffer containing Tris-HCl and sucrose in distilled water. A protein assay was performed on the resuspended cell suspension and used in radio-receptor binding assays.

Radio-Receptor Assay

The binding of synthetic salmonid SS-25 (SEQ ID NO:16), mammalian SS-14 (Sigma) SEQ ID NO:1) and mammalian SS-28 (Ser-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys) (SEQ ID NO:21) to cloned human somatostatin receptor subtype 1 was evaluated. The receptor binding assays were performed substantially as described in Pesek et al., *J. of Endocrinol.*, 150, 179–186 (1996). Briefly, cell membranes, 25–1000 $\mu$g, were added to two sets of tubes labeled for total and non-specific binding (in triplicate) containing the following reagents in a final volume of 300 $\mu$l. The total binding tubes contained the microsomal membrane preparation, $^{125}$I-[Tyr1]-SS-14, and assay buffer, whereas the non-specific binding tubes contained the microsomal membrane preparation, $^{125}$I-[Tyr11]-SS-14, non-radiolabeled hormone, and assay buffer.

All tubes were incubated for 30–60 minutes at 37° C. while shaking. Reactions were stopped by adding 1 ml of ice-cold assay buffer and centrifuged at 20,000×g for 15 minutes. The supernatant is aspirated off. The resulting pellets were washed once with ice-cold assay buffer and centrifuged again at 20,000×g for 15 minutes. Again, the supernatant was aspirated off. The resulting pellets were counted in a gamma counter to determine the binding properties of the various ligands to the somatostatin receptor.

The results, shown in FIG. 8, indicate that the human somatostatin receptor type 1 has a greater affinity for salmonid SS-25 (SEQ ID NO:16) than for either mammalian SS-14 (SEQ ID NO: 1) or mammalian SS-28 (SEQ ID NO:21).

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. An isolated or purified somatostatin polypeptide comprising a polypeptide selected from the group consisting of:
   (a) a polypeptide comprising SEQ ID NO:15;
   (b) a subunit of the polypeptide of (a) comprising SEQ ID NO:16 and at least 7 contiguous amino acids from SEQ ID NO:17; and
   (c) an analog of the polypeptide of (a) that has an amino acid sequence at least about 85% identical to SEQ ID NO:15;
   wherein the somatostatin polypeptide binds to a somatostatin receptor.

2. The somatostatin polypeptide of claim 1, wherein the somatostatin polypeptide comprises at least one amino acid sequence selected from the group consisting of SEQ ID NOs:2, 16, 17, 18, and 19.

3. An isolated or purified polypeptide comprising at least one amino acid sequence selected from the group consisting of SEQ ID NOs:15, 17, and 19.

4. A fusion polypeptide comprising an N-terminal somatostatin region comprising at least one first amino acid sequence comprising a somatostatin polypeptide of claim 1 covalently linked to a C-terminal region comprising a second amino acid sequence.

5. The fusion polypeptide of claim 4 wherein the second amino acid sequence encodes a bioactive moiety.

6. The fusion polypeptide of claim 4 wherein the first amino acid sequence comprises at least one amino acid sequence selected from the group consisting of NOs: 15, 16, 17, 18, and 19.

7. The fusion polypeptide of claim 5 wherein the first amino acid sequence comprises SEQ ID NO:18.

* * * * *